United States Patent
Yin et al.

(10) Patent No.: US 12,358,987 B2
(45) Date of Patent: Jul. 15, 2025

(54) ANTI-CD47/ANTI-PD-1 BISPECIFIC ANTIBODY, PREPARATION METHOD AND USE THEREOF

(71) Applicant: Nanjing GenScript Biotech Co., Ltd., Nanjing (CN)

(72) Inventors: Liusong Yin, Nanjing (CN); Zhongdao Li, Nanjing (CN); Tielin Zhou, Singapore (SG); Zhuo Fang, Nanjing (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 869 days.

(21) Appl. No.: 17/624,031

(22) PCT Filed: Jul. 8, 2020

(86) PCT No.: PCT/CN2020/100845
§ 371 (c)(1),
(2) Date: Dec. 30, 2021

(87) PCT Pub. No.: WO2021/004480
PCT Pub. Date: Jan. 14, 2021

(65) Prior Publication Data
US 2022/0332824 A1 Oct. 20, 2022

(30) Foreign Application Priority Data
Jul. 8, 2019 (CN) .......................... 201910609431.0

(51) Int. Cl.
*C07K 16/28* (2006.01)
*A61P 35/00* (2006.01)

(52) U.S. Cl.
CPC .......... *C07K 16/2818* (2013.01); *A61P 35/00* (2018.01); *C07K 16/2803* (2013.01); *C07K 2317/31* (2013.01); *C07K 2317/53* (2013.01); *C07K 2317/565* (2013.01); *C07K 2317/569* (2013.01); *C07K 2317/76* (2013.01); *C07K 2317/92* (2013.01)

(58) Field of Classification Search
CPC ............ C07K 16/2818; C07K 16/2803; C07K 2317/31; C07K 2317/53; C07K 2317/565; C07K 2317/569; C07K 2317/76; C07K 2317/92; C07K 2317/52; C07K 2317/522; C07K 2317/524; C07K 2319/00; A61P 35/00
See application file for complete search history.

(56) References Cited

U.S. PATENT DOCUMENTS

2019/0144543 A1 5/2019 Chen et al.
2020/0317787 A1 10/2020 Li et al.

FOREIGN PATENT DOCUMENTS

| CN | 109897111 A | 6/2019 | |
|---|---|---|---|
| WO | WO-2007014278 A2 * | 2/2007 | ........... A61K 39/395 |
| WO | WO-2016024021 A1 * | 2/2016 | ......... A61K 47/6811 |
| WO | WO 2018/014260 A1 | 1/2018 | |
| WO | WO-2019129053 A1 * | 7/2019 | ......... A61K 47/6813 |
| WO | WO-2019137541 A1 * | 7/2019 | .............. A61P 35/00 |
| WO | WO-2019144895 A1 * | 8/2019 | .............. A61P 35/00 |
| WO | WO 2019/179434 A1 | 9/2019 | |
| WO | WO-2023049867 A1 * | 3/2023 | |
| WO | WO-2023241656 A1 * | 12/2023 | .............. A61P 35/00 |

OTHER PUBLICATIONS

Sela-Culang, Kunik and Ofran. The structural basis of antibody-antigen recognition. Frotiers in Immunology. vol. 4, Article 302, Oct. 2013 (Year: 2013).*
Koenig et al. Mutational landscape of antibody variable domains reveals a switch modulating the interdomain conformational dynamics and antigen binding. PNAS. E486-E495, Jan. 5, 2017 (Year: 2017).*
Herold et al. Determinants of the assembly and functions of antibody variable domains. Nature Scientific Reports. 7:12276, Sep. 25, 2017 (Year: 2017).*
International Search Report and Written Opinion mailed on Oct. 12, 2020 in International Application No. PCT/CN2020/100845 (Chinese) (8 pages).
English translation of International Search Report mailed on Oct. 12, 2020 in International Application No. PCT/CN2020/100845 (2 pages).
Extended European Search Report dated Jul. 10, 2023 in European Patent Application No. 20836694.8 (11 pages).

* cited by examiner

*Primary Examiner* — Joanne Hama
*Assistant Examiner* — Amy M. Chattin
(74) *Attorney, Agent, or Firm* — Klarquist Sparkman, LLP

(57) ABSTRACT

The present invention relates to an anti-CD47/anti-PD-1 bispecific antibody, preparation method thereof and use thereof. The bispecific antibody includes (a) a first antigen binding portion including a heavy chain variable region (Vn) and a light chain variable region (Vl), wherein Vn and Vl form an antigen binding site that specifically binds to CD47; and (b) a second antigen binding portion including a single-domain antibody (sdAb) that specifically binds to PD-1, wherein the first antigen binding portion and the second antigen binding portion are fused with each other. The bispecific antibody of the present invention can block two manners of tumor immune escape simultaneously, and thus, has a good effect in tumor immunotherapy.

18 Claims, 3 Drawing Sheets
Specification includes a Sequence Listing.

ANTI-CD47/ANTI-PD-1 BISPECIFIC ANTIBODY, PREPARATION METHOD AND USE THEREOF

CROSS REFERENCE TO RELATED APPLICATIONS

This is the U.S. National Stage of International Application No. PCT/CN2020/100845, filed Jul. 8, 2020, which was published in Chinese, which in turn claims the benefit of CN 201910609431.0, filed Jul. 8, 2019.

TECHNICAL FIELD

The present invention relates to the field of antibodies, and specifically, to a bispecific antibody, a preparation method thereof, and use thereof. The bispecific antibody includes a first antigen binding portion that specifically binds to CD47 and a second antigen binding portion that specifically binds to PD-1.

BACKGROUND

The mammalian immune system is a host defense system that protects a mammal from microbial infections and cancers. (Chen et al., Frontiers Immunol. 9:320 (2018)) The immune system all over the body is an extremely complex network system. Different immune cells and specific tissues and organs exert a synergistic effect to form the immune system. When the immune system is functioning normally, diseased cells in the host body will be recognized from healthy cells and eliminated, thereby ensuring the stability of the body's environment. Therefore, maintaining the integrity of the immune system is essential to maintaining our own health. Conversely, loss of control of the immune system will cause autoimmune diseases, inflammation, cancers, etc (Ribas et al., Cancer Discovery 5:915-9 (2015); Yao and Chen, Eur. J. Immunol. 43:576-9 (2013)). The immune system can be divided into two categories, namely humoral immunity and cell-mediated immunity. Antibodies and other biological macromolecules regulate humoral immunity. In contrast, cell-mediated immunity is regulated at the cellular level, involving the activation of macrophages, natural killer cells, and antigen-specific killer T cells.

Activation and suppression of immune response are mainly regulated by two independent signaling pathways (Gorentla and Zhong, J. Clin. Cell. Immunol. (2012); Huse, J. Cell Sci. 122:1269-73 (2009); Mizota et al., J. Anesthesia 27:80-7 (2013)). The first signal is antigen-mediated. The first signal is generated when the T-cell receptor specifically recognizes and binds to the antigen peptide presented by the MHC on the surface of the antigen-presenting cell (APC). The second signal is provided by the interaction between the APCs and costimulators expressed on the surface of T cells. T cells can kill tumors only when the first and second signals are activated in turn. If the second signal is lacking, T cells will enter a state of unresponsiveness or will be immune tolerance, and even cause programmed cell death.

As described above, the second signaling pathway is very important to the activation of immune cells. Specifically, co-stimulatory and co-inhibitory receptors participate in the second signaling pathway to perform immune response and regulation on antigen-receptor presentation and balance positive and negative signals while maintaining immune tolerance to autoantigens, maximizing the immune response to invaders (Chen and Flies, Nat. Rev. Immunol. 13:227-42 (2013); Ewing et al., Int. J. Cardiol. 168:1965-74 (2013); Liu et al., Immunol. Invest. 45:813-31 (2016); Shen et al., Frontiers in Biosci. 24:96-132 (2019); Zhang and Vignali, Immunity 44:1034-51 (2016)).

CD28 is a member of the CD28 family and is a major T-cell co-stimulatory receptor, constitutively expressed on initial $CD4^+$ and $CD8^+$ T cells. CD28 receptor ligands include CD80, CD86, programmed death-ligand 1 (PD-L1), programmed death-ligand 2 (PD-L2), etc. PD-1 is a transmembrane protein that binds to the inhibitory checkpoint molecule of PD-1 and suppresses the adaptive immune response by transmitting the inhibitory "don't find me" signal. The PD-1/PD-L1 signaling pathway plays a vital role in the development of immune tolerance, preventing overreaction of the immune system, thereby avoiding autoimmune diseases. However, this is usually deregulated as the cancer progresses, allowing tumor cells to bypass protective mechanisms by disguising themselves as healthy tissue. Tumor cells overexpressing PD-L1 can evade T cell-mediated death by activating the inhibitory PD-1/PD-L1 signaling pathway, inhibiting the anti-tumor adaptive immune response. Overexpression of PD-1 in human tumor-associated macrophages (TAMS) is also shown to inhibit phagocytosis and tumor immunity. Currently, the anti-PD-1 or anti-PD-L1 monoclonal antibody that blocks the interaction of PD-1/PD-L1 has a significant effect in cancer treatment. Although the United States Food and Drug Administration approved anti-PD-1 or anti-PD-L1 monoclonal antibody such as keytruda, opdivo, and tecentriq for the treatment of advanced cancers, these anti-tumor drugs only respond to some patients, which implies that the blockade of a single inhibitory signaling pathway is not enough to activate the immune response, and there are other mechanisms to suppress the immune system.

CD47, also known as integrin associated protein, is a transmembrane protein that is encoded by the CD47 gene, and belongs to the immunoglobulin superfamily CD47 is widely expressed on the surface of normal cells and can interact with signal-regulatory protein alpha (SIRPα), thrombospondin-1 (TSP-1), and integrin to mediate cell apoptosis, proliferation, and immunity responses, and the like. CD47, as an innate immune checkpoint receptor, binds to SIRPα mainly expressed on macrophages and dendritic cells and then releases a "don't eat me" signal to the macrophages to inhibit phagocytosis, thereby avoiding the attack of the body's immune system. Cancer cells escape phagocytosis by upregulating the expression of CD47, thereby evading immune surveillance. The overexpression of CD47 in blood and solid tumors is highly correlated with the poor prognosis of clinical treatment. Therefore, the use of anti-CD47 antibodies or high-affinity SIRPα variants to block the CD47-SIRPα signaling pathway has become a potential strategy to promote the phagocytosis of tumor cells by macrophages. However, in view of the wide expression of CD47, the anti-CD47 antibodies have a high risk of binding to healthy cells, especially red blood cells, which will increase the risk of blood toxicity. In addition, more and more studies have shown that blocking CD47 alone is not sufficient to generate anti-tumor immunity in immunocompetent hosts. Moreover, researchers at Stanford University reported that the interference in the CD47/SIRPα pathway by SIRPα treatment cannot induce phagocytosis (Sockolosky et al., PNAS 113:E2646-2654 (2016)). Therefore, considering the effectiveness and safety of cancer treatment, the anti-CD47 antibodies need to be further optimized to improve tumor targeting specificity.

SUMMARY

In one aspect, the present invention provides an isolated bispecific binding protein, and the protein includes a first antigen binding portion that specifically binds to CD47 and a second antigen binding portion that specifically binds to PD-1. Specifically, the present invention provides an isolated anti-CD47/anti-PD-1 bispecific antigen-binding protein or a fragment thereof, including (a) a first antigen binding portion including a heavy chain variable region ($V_H$) and a light chain variable region ($V_L$), $V_H$ and $V_L$ forming an antigen binding site that specifically binds to CD47; and (b) a second antigen binding portion including a single-domain antibody (sdAb) that specifically binds to PD-1, where the first antigen binding portion and the second antigen binding portion are fused to each other.

In some embodiments, the $V_H$ of the first antigen binding portion includes heavy chain complementarity-determining regions HCDR1, HCDR2, and HCDR3, and the amino acid sequences of the HCDR1, HCDR2 and HCDR3 are respectively as set forth in SEQ ID NO:33, SEQ ID NO:34, and SEQ ID NO:35, or the sequences respectively including at most three (three, two or one) amino acid mutations thereto; and the $V_L$ of the first antigen binding portion includes light chain complementarity-determining regions LCDR1, LCDR2 and LCDR3, the amino acid sequences of the LCDR1, LCDR2, and LCDR3 are respectively as set forth in SEQ ID NO:36, SEQ ID NO:37, and SEQ ID NO:38, or the sequences respectively including at most three (three, two or one) amino acid mutations thereto. In some embodiments, the $V_H$ of the first antigen binding portion includes heavy chain complementarity-determining regions HCDR1, HCDR2, and HCDR3, the amino acid sequences of the HCDR1, HCDR2, and HCDR3 are respectively as set forth in SEQ ID NO:33, SEQ ID NO:34, and SEQ ID NO:35, or the sequences respectively including at most three (three, two or one) amino acid substitutions thereto; and the $V_L$ of the first antigen binding portion includes light chain complementarity-determining regions LCDR1, LCDR2, and LCDR3, the amino acid sequences of the LCDR1, LCDR2, and LCDR3 are respectively as set forth in SEQ ID NO:36, SEQ ID NO:37, and SEQ ID NO:38, or the sequences respectively including at most three (three, two or one) amino acid substitutions thereto. In some embodiments, the $V_H$ of the first antigen binding portion includes heavy chain complementarity-determining regions HCDR1, HCDR2, and HCDR3, and the amino acid sequences of the HCDR1, HCDR2, and HCDR3 are respectively as set forth in SEQ ID NO:33, SEQ ID NO:34, and SEQ ID NO:35; and the $V_L$ of the first antigen binding portion includes light chain complementarity-determining regions LCDR1, LCDR2, and LCDR3, and the amino acid sequences of the LCDR1, LCDR2, and LCDR3 are respectively as set forth in SEQ ID NO:36, SEQ ID NO:37, and SEQ ID NO:38.

In some embodiments, the single domain antibody of the second antigen binding portion includes the complementarity-determining regions CDR1, CDR2 and CDR3, the amino acid sequence of CDR1 is as set forth in SEQ ID NO:39 or SEQ ID NO:42, or the sequence including at most three (three, two or one) amino acid mutations thereto, the amino acid sequence of CDR2 is as set forth in SEQ ID NO:40 or SEQ ID NO:43, or the sequence including at most three (three, two or one) amino acid mutations thereto, and the amino acid sequence of CDR3 is as set forth in SEQ ID NO:41 or SEQ ID NO:44, or the sequence including at most three (three, two or one) amino acid mutations thereto. In some embodiments, the single domain antibody of the second antigen binding portion includes complementarity-determining regions CDR1, CDR2 and CDR3, the amino acid sequence of CDR1 is as set forth in SEQ ID NO:39 or SEQ ID NO:42, or the sequence including at most three (three, two or one) amino acid substitutions thereto, the amino acid sequence of CDR2 is as set forth in SEQ ID NO:40 or SEQ ID NO:43, or the sequence including at most three (three, two or one) amino acid substitutions thereto, and the amino acid sequence of CDR3 is as set forth in SEQ ID NO:41 or SEQ ID NO:44, or the sequence including at most three (three, two or one) amino acid substitutions thereto. In some specific embodiments, the single domain antibody of the second antigen binding portion includes complementarity-determining regions CDR1, CDR2 and CDR3, the amino acid sequence of CDR1 is as set forth in SEQ ID NO:39 or SEQ ID NO:42, the amino acid sequence of CDR2 is as set forth in SEQ ID NO:40 or SEQ ID NO:43, and the amino acid sequence of CDR3 is as set forth in SEQ ID NO:41 or SEQ ID NO:44. In some embodiments, the single domain antibody of the second antigen binding portion includes complementarity-determining regions CDR1, CDR2 and CDR3, amino acid sequences of the complementarity-determining regions CDR1, CDR2 and CDR3 are respectively as set forth in SEQ ID NO:39, SEQ ID NO:40, and SEQ ID NO:41, or the sequences respectively including at most three (three, two, or one) amino acid substitutions thereto. In some embodiments, the single domain antibody of the second antigen binding portion includes complementarity-determining regions CDR1, CDR2, and CDR3, amino acid sequences of the complementarity-determining regions CDR1, CDR2, and CDR3 are respectively as set forth in SEQ ID NO:42, SEQ ID NO:43, and SEQ ID NO:44, or the sequences respectively including at most three (three, two or one) amino acid substitutions thereto. In some specific embodiments, the single domain antibody of the second antigen binding portion includes complementarity-determining regions CDR1, CDR2 and CDR3, and amino acid sequences of the complementarity-determining regions CDR1, CDR2 and CDR3 are respectively as set forth in SEQ ID NO:39, SEQ ID NO:40, and SEQ ID NO:41. In some specific embodiments, the single domain antibody of the second antigen binding portion includes complementarity-determining regions CDR1, CDR2 and CDR3, and amino acid sequences of the complementarity-determining regions CDR1, CDR2 and CDR3 are respectively as set forth in SEQ ID NO:42, SEQ ID NO:43, and SEQ ID NO:44.

In some embodiments, the first antigen binding portion is a full-length antibody including two heavy chains and two light chains, the heavy chain includes $V_H$, and the light chain includes $V_L$.

In some embodiments, the first antigen binding portion and the second antigen binding portion are fused. In some specific embodiments, the C-terminus of the second antigen binding portion is fused to the N-terminus of at least one heavy chain of the first antigen binding portion or the N-terminus of at least one light chain of the first antigen binding portion. In some embodiments, the N-terminus of the second antigen binding portion is fused to the C-terminus of at least one heavy chain of the first antigen binding portion or the C-terminus of at least one light chain of the first antigen binding portion.

In some embodiments, the first antigen binding portion and the second antigen binding portion are fused by a peptide bond or a peptide linker. In some embodiments, the peptide linker is selected from a mutated human IgG1 hinge region or a GS linker. In some preferred embodiments, the amino acid sequence of the peptide linker is as set forth in SEQ ID NO:46 or SEQ ID NO:48.

In some embodiments, the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6. In some embodiments, the heavy chain of the first antigen binding portion includes a sequence that is at least 95% identical to the amino acid sequence as set forth in SEQ ID NO:4, and the light chain of the first antigen binding portion includes a sequence that is at least 95% identical to the amino acid sequence as set forth in SEQ ID NO:6. In some specific embodiments, the heavy chain of the first antigen binding portion includes the amino acid sequence as set forth in SEQ ID NO:4, and the light chain of the first antigen binding portion includes the amino acid sequence as set forth in SEQ ID NO:6.

In some embodiments, the second antigen binding portion includes a sequence that is at least 80%, 85%, 90%, 95%, 96%, 97%, 98%, or 99% identical to the amino acid sequence as set forth in SEQ ID NO:30 or SEQ ID NO:32. In some embodiments, the second antigen binding portion includes a sequence that is at least 95% identical to the amino acid sequence as set forth in SEQ ID NO:30. In some embodiments, the second antigen binding portion includes a sequence that is at least 95% identical to the amino acid sequence as set forth in SEQ ID NO:32. In some specific embodiments, the second antigen binding portion includes the amino acid sequence as set forth in SEQ ID NO:30. In some specific embodiments, the second antigen binding portion includes the amino acid sequence as set forth in SEQ ID NO:32.

In some embodiments, an isolated anti-CD47/anti-PD-1 bispecific antigen-binding protein or a fragment thereof is provided, the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6; and the second antigen binding portion includes a sequence that is at least 80%, 85%, 90%, 95%, 96%, 97%, 98%, or 99% identical to the amino acid sequence as set forth in SEQ ID NO:30 or SEQ ID NO:32. In some embodiments, an isolated anti-CD47/anti-PD-1 bispecific antigen-binding protein or a fragment thereof is provided; the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6; and the second antigen binding portion includes a sequence that is at least 80%, 85%, 90%, 95%, 96%, 97%, 98%, or 99% identical to the amino acid sequence as set forth in SEQ ID NO:30. In some specific embodiments, in the isolated anti-CD47/anti-PD-1 bispecific antigen-binding protein or a fragment thereof, the heavy chain of the first antigen binding portion includes the amino acid sequence as set forth in SEQ ID NO:4, and the light chain of the first antigen binding portion includes the amino acid sequence as set forth in SEQ ID NO:6; and the second antigen binding portion includes the amino acid sequence as set forth in SEQ ID NO:30. In some embodiments, an isolated anti-CD47/anti-PD-1 bispecific antigen-binding protein or a fragment thereof is provided, the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6; and the second antigen binding portion includes a sequence that is at least 80%, 85%, 90%, 95%, 96%, 97%, 98%, or 99% identical to the amino acid sequence as set forth in SEQ ID NO:32. In some specific embodiments, in the isolated anti-CD47/anti-PD-1 bispecific antigen-binding protein or a fragment thereof, the heavy chain of the first antigen binding portion includes the amino acid sequence as set forth in SEQ ID NO:4, and the light chain of the first antigen binding portion includes the amino acid sequence as set forth in SEQ ID NO:6; and the second antigen binding portion includes the amino acid sequence as set forth in SEQ ID NO:32.

In some embodiments, the first antigen binding portion includes a human, humanized, or chimeric antibody or a fragment thereof. In some embodiments, the second antigen binding portion includes a single domain antibody that specifically binds to PD-1, and the sdAb is a camelid, chimeric, humanized, or human antibody.

In some embodiments, an isolated anti-CD47/anti-PD-1 bispecific antigen-binding protein or a fragment thereof is provided, including an anti-CD47 antibody and an anti-PD-1 single domain antibody, with the N-terminus of the anti-PD-1 single domain antibody fused to the C-terminus of two heavy chains of the anti-CD47 antibody, wherein the heavy chain fusion polypeptide includes a sequence that is at least 80%, 85%, 90%, 95%, 96%, 97%, 98%, or 99% identical to the amino acid sequence as set forth in SEQ ID NO:8, SEQ ID NO:10, or SEQ ID NO: 24, and the light chain polypeptide includes a sequence that is at least 80%, 85%, 90%, 95%, 96%, 97%, 98%, or 99% identical to the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two heavy chains of the anti-CD47 antibody, wherein the heavy chain fusion polypeptide includes the amino acid sequence as set forth in SEQ ID NO:8, SEQ ID NO: 10, or SEQ ID NO:24, and the light chain polypeptide includes the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two heavy chains of the anti-CD47 antibody, wherein the heavy chain fusion polypeptide includes the amino acid sequence as set forth in SEQ ID NO:8, and the light chain polypeptide includes the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two heavy chains of the anti-CD47 antibody, wherein the heavy chain fusion polypeptide includes the amino acid sequence as set forth in SEQ ID NO: 10, and the light chain polypeptide includes the amino acid sequence as set forth in SEQ ID NO: 6. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two heavy chains of the anti-CD47 antibody, wherein the heavy chain fusion polypeptide includes the amino acid sequence as set forth in SEQ ID NO:24, and the light chain polypeptide includes the amino acid sequence as set forth in SEQ ID NO:6.

In some embodiments, another isolated anti-CD47/anti-PD-1 bispecific antigen-binding protein or a fragment thereof is provided, including an anti-CD47 antibody and an anti-PD-1 single domain antibody, with the C-terminus of the anti-PD-1 single domain antibody fused to the N-terminus of two heavy chains of the anti-CD47 antibody, wherein the heavy chain fusion polypeptide includes a sequence that is at least 80%, 85%, 90%, 95%, 96%, 97%, 98%, or 99% identical to the amino acid sequence as set forth in SEQ ID NO:12 or SEQ ID NO:14, and the light chain polypeptide includes a sequence that is at least 80%, 85%, 90%, 95%, 96%, 97%, 98%, or 99% identical to the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two heavy chains of the anti-CD47 antibody, wherein the heavy chain fusion polypeptide includes the amino acid sequence as set forth in SEQ ID NO:12 or SEQ ID NO:14, and the light chain polypeptide includes the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two heavy chains of the anti-CD47 antibody, wherein the heavy chain fusion polypeptide includes the amino acid sequence as set forth in SEQ ID NO:12, and the light chain polypeptide includes the amino acid sequence as set forth in SEQ ID NO:6. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two heavy chains of the anti-CD47 antibody, wherein the heavy chain fusion polypeptide includes the amino acid sequence as set forth in SEQ ID NO:14, and the light chain polypeptide includes the amino acid sequence as set forth in SEQ ID NO:6.

In some embodiments, an isolated anti-CD47/anti-PD-1 bispecific antigen-binding protein or a fragment thereof is provided, including an anti-CD47 antibody and an anti-PD-1 single domain antibody, with the N-terminus of the anti-PD-1 single domain antibody fused to the C-terminus of two light chains of the anti-CD47 antibody, wherein the light chain fusion polypeptide includes a sequence that is at least 80%, 85%, 90%, 95%, 96%, 97%, 98%, or 99% identical to the amino acid sequence as set forth in SEQ ID NO:16 or SEQ ID NO:18, and the heavy chain polypeptide includes a sequence that is at least 80%, 85%, 90%, 95%, 96%, 97%, 98%, or 99% identical to the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two light chains of the anti-CD47 antibody, wherein the light chain fusion polypeptide includes the amino acid sequence as set forth in SEQ ID NO:16 or SEQ ID NO:18, and the heavy chain polypeptide includes the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two light chains of the anti-CD47 antibody, wherein the light chain fusion polypeptide includes the amino acid sequence as set forth in SEQ ID NO:16, and the heavy chain polypeptide includes the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the N-terminus of the anti-PD-1 single domain antibody fused to the C-terminus of two light chains of the anti-CD47 antibody, wherein the light chain fusion polypeptide includes the amino acid sequence as set forth in SEQ ID NO:18, and the heavy chain polypeptide includes the amino acid sequence as set forth in SEQ ID NO:4.

In some embodiments, another isolated anti-CD47/anti-PD-1 bispecific antigen-binding protein or a fragment thereof is provided, including an anti-CD47 antibody and an anti-PD-1 single domain antibody, with the C-terminus of the anti-PD-1 single domain antibody fused to the N-terminus of two light chains of the anti-CD47 antibody, wherein the light chain fusion polypeptide includes a sequence that is at least 80%, 85%, 90%, 95%, 96%, 97%, 98%, or 99% identical to the amino acid sequence as set forth in SEQ ID NO:20 or SEQ ID NO:22, and the heavy chain polypeptide includes a sequence that is at least 80%, 85%, 90%, 95%, 96%, 97%, 98%, or 99% identical to the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two light chains of the anti-CD47 antibody, wherein the light chain fusion polypeptide includes the amino acid sequence as set forth in SEQ ID NO:20 or SEQ ID NO:22, and the heavy chain polypeptide includes the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two light chains of the anti-CD47 antibody, wherein the light chain fusion polypeptide includes the amino acid sequence as set forth in SEQ ID NO:20, and the heavy chain polypeptide includes the amino acid sequence as set forth in SEQ ID NO:4. In some specific embodiments, the isolated anti-CD47/anti-PD-1 bispecific antigen-binding protein or a fragment thereof includes an anti-CD47 antibody and an anti-PD-1 single domain antibody, with the C-terminus of the anti-PD-1 single domain antibody fused to the N-terminus of two light chains of the anti-CD47 antibody, wherein the light chain fusion polypeptide includes the amino acid sequence as set forth in SEQ ID NO:22, and the heavy chain polypeptide includes the amino acid sequence as set forth in SEQ ID NO:4.

In another aspect, the present invention provides an isolated polynucleotide encoding the anti-CD47/anti-PD-1 bispecific antigen-binding protein or the fragment thereof. It can be commonly known to those skilled in the art that the change (such as substitution or deletion) of sequences encoding the protein does not change the amino acid of the protein. In some embodiments, the polynucleotide encoding the heavy chain fusion protein of the anti-CD47/anti-PD-1 bispecific antigen-binding protein or the fragment thereof includes a sequence that is at least 80%, 85%, 90%, 95%, 96%, 97%, 98%, or 99% identical to the nucleotide sequence as set forth in SEQ ID NO:7, SEQ ID NO:9, SEQ ID NO:11, SEQ ID NO:13, or SEQ ID NO:23, and the polynucleotide encoding the light chain of the anti-CD47/anti-PD-1 bispecific antigen-binding protein or the fragment thereof includes a sequence that is at least 80%, 85%, 90%, 95%, 96%, 97%, 98%, or 99% identical to the nucleotide sequence as set forth in SEQ ID NO:5. In some specific embodiments, the polynucleotide encoding the heavy chain fusion protein of the anti-CD47/anti-PD-1 bispecific antigen-binding protein or the fragment thereof includes the nucleotide sequence as set forth in SEQ ID NO:7, SEQ ID NO:9, SEQ ID NO:11, SEQ ID NO:13, or SEQ ID NO:23, and the polynucleotide encoding the light chain of the anti-CD47/anti-PD-1 bispecific antigen-binding protein or the fragment thereof includes the nucleotide sequence as set forth in SEQ ID NO:5. In some embodiments, the polynucleotide encoding the light chain fusion protein of the anti-CD47/anti-PD-1 bispecific antigen-binding protein or the fragment thereof includes a sequence that is at least 80%, 85%, 90%, 95%, 96%, 97%, 98%, or 99% identical to the nucleotide sequence as set forth in SEQ ID NO:15, SEQ ID NO:17, SEQ ID NO:19, or SEQ ID NO:21, and the polynucleotide encoding the heavy chain of the anti-CD47/anti-PD-1 bispecific antigen-binding protein or the fragment thereof includes a sequence that is at least 80%, 85%, 90%, 95%, 96%, 97%, 98%, or 99% identical to the nucleotide sequence as set forth in SEQ ID NO:3. In some specific embodiments, the polynucleotide encoding the light chain fusion protein of the anti-CD47/anti-PD-1 bispecific antigen-binding protein or the fragment thereof includes the nucleotide sequence as set forth in SEQ ID NO:15, SEQ ID NO:17, SEQ ID NO:19, or SEQ ID NO:21, and the polynucleotide encoding the heavy chain of the anti-CD47/anti-PD-1 bispecific antigen-binding protein or the fragment thereof includes the nucleotide sequence as set forth in SEQ ID NO:3.

Further, a vector including the isolated polynucleotide encoding the isolated anti-CD47/anti-PD-1 bispecific antigen-binding protein or the fragment thereof is provided. It can be commonly known to those skilled in the art that a vector is a plasmid, a phage vector, or a viral vector. In some specific embodiments, the vector is a recombinant expression vector, for example, a plasmid. These vectors include various elements to support the functions thereof as conventional expression vectors, for example, including promoters, ribosome binding elements, terminators, enhancers, selective markers, and origins of replication. The promoters may be conventional promoters, inducible promoters, or repressible promoters. It can be commonly known in the art that many expression vectors can deliver nucleic acids into cells and can be used to produce antibodies or antigen-binding fragments thereof in cells. According to the method in the examples of the present invention, conventional cloning techniques or artificial gene synthesis can be used to produce recombinant expression vectors.

Further, a host cell including the isolated polynucleotide or the vector is provided. In the present invention, any host cell conventional in the art can be used for the expression of antibodies or antigen-binding fragments thereof. In some embodiments, the host cell is *E. coli* TG1 or BL21 (used to express scFv or Fab antibodies), CHO-DG44, CHO-3E7, CHO-K1, or HEK293. According to specific examples, the recombinant expression vector is transfected into the host cell by a conventional method (such as chemical transfection, thermal transfection, or electrotransfection), and is stably integrated into the host cell genome, so that the recombinant nucleic acids can be effectively expressed.

In another aspect, the present invention provides a method for producing an isolated anti-CD47/anti-PD-1 bispecific antigen-binding protein or a fragment thereof, including culturing the host cell including the polynucleotide encoding the bispecific antigen-binding protein or the fragment thereof in the present invention under proper conditions, and recovering an antibody or a fragment thereof from the cell or a cell culture medium. The expression antibody or the fragment thereof may be obtained from cells or extracted and purified by conventional methods in the art.

In another aspect, the present invention provides a pharmaceutical composition, including the isolated anti-CD47/anti-PD-1 bispecific antigen-binding protein or the fragment thereof and a pharmaceutically acceptable carrier. The "pharmaceutically acceptable carrier" refers to a solid or liquid diluent, a filler, an antioxidant, a stabilizer, or other substances that can be administered safely, suitable for human and/or animal administration without excessive side effects, and also suitable for maintaining the activity of drugs or active agents therein. Different carriers well known in the art may be administered according to the route of administration, including but not limited to, carbohydrates, starch, cellulose and derivatives thereof, maltose, gelatin, talc, calcium sulfate, vegetable oils, synthetic oils, polyols, alginic acid, phosphate buffers, emulsifiers, isotonic saline, and/or pyrogen-free water. The pharmaceutical composition provided in the present invention may be prepared into clinically acceptable dosage forms such as powders and injections. Any proper route may be used to administer the pharmaceutical composition of the present invention to subjects, for example, it may be administered by oral, intravenous infusion, intramuscular injection, subcutaneous injection, subperitoneal, rectal, sublingual, inhalation, or transdermal.

In another aspect, the present invention provides a method for treating subjects suffering from or at risk of suffering from diseases related to abnormal expression of CD47 and/or PD-1, including administering the pharmaceutical composition with an effective amount to the subjects.

In another aspect, the present invention provides use of the anti-CD47/anti-PD-1 bispecific antigen-binding protein or the fragment thereof, the polynucleotide, the vector, and the host cell in preparing medicines for diseases related to abnormal expression of CD47 and/or PD-1.

In some embodiments, the diseases related to CD47 and/or PD-1 are cancers. In some embodiments, the cancers are solid tumors, such as colorectal cancer, non-small cell lung cancer, small cell lung cancer, renal cell cancer, ovarian cancer, breast cancer, pancreatic cancer, stomach cancer, bladder cancer, esophageal cancer, mesothelioma, melanoma, head and neck cancer, Hodgkin lymphoma, hepatocellular carcinoma, advanced kidney cancer, urothelial carcinoma, and cervical cancer. In a preferred embodiment, the cancers are solid tumors, such as pancreatic cancer, non-small cell lung cancer, melanoma, breast cancer, stomach cancer, colorectal cancer, head and neck cancer, Hodgkin lymphoma, hepatocellular carcinoma, advanced kidney cancer, urothelial carcinoma, and cervical cancer.

In some embodiments, the method further includes administering additional tumor treatment to the subjects, such as surgery, radiation therapy, chemotherapy, immunotherapy, hormone therapy, or a combination thereof.

In the present invention, the PD-1 single domain antibody is linked to the terminus of the heavy chain or light chain of the anti-CD47 monoclonal antibody in a specific way, the produced anti-CD47/anti-PD-1 bispecific antigen-binding protein has significantly increased affinity for PD-1 antigen, and the bispecific antibody also has significantly increased biological activity for blocking PD-1, indicating that the increased affinity of the bispecific antibody to the PD-1 antigen can enhance the corresponding biological activity. In addition, this bispecific antibody can also block the CD47 signaling pathway, so that it can block two manners of tumor immune escape at the same time.

Explanation of Terms

An "antigen-binding protein fragment" means a fragment of an antibody and an antibody mimetic, generally including at least part of the antigen binding regions or variable regions (for example, one or more CDRs) of a parental antibody. The antibody fragment retains at least some of the binding specificity of the parental antibody. For example, the antigen-binding protein fragment that can bind to CD47 or part of it includes but not limited to sdAb (single domain antibody), Fab (for example, obtained by papain digestion of antibodies), F(ab')$_2$ (for example, obtained by pepsin digestion), and Fv or scFv (for example, obtained by molecular biology techniques).

"single domain antibody (sdAb)" refers to single antigen-binding polypeptide with three complementarity-determining regions (CDRs). The sdAb can bind to the antigen independently without pairing with corresponding CDR-containing polypeptide. In some cases, sdAb is artificially engineered from camelid heavy chain antibodies and is referred to as a "V$_H$H domain". Cartilaginous fishes also have heavy chain antibodies (immunoglobulin new antigen receptor (IgNAR)), and sdAb referred to as a "V$_{NAR}$ domain" may also be produced from this class of antibodies. Camelid sdAb is a smallest known antigen-binding antibody fragment (Refer to e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). The basic V$_H$H has the following structure from the N-terminus to the C-terminus: FR1-CDR1-FR2-CDR2-FR3-CDR3-FR4, where FR1 to FR4 are framework regions 1 to 4, and CDR1 to CDR3 are CDRs 1 to 3. The anti-PD-1 sdAb in the present invention refers to sdAb that can specifically bind to PD-1, in particular, sdAb that can bind to human PD-1. The anti-PD-1 sdAb in the present invention may be selected from the anti-PD-1 sdAb specifically described in the patent application PCT/CN2019/071691. The construction, expression, extraction, and purification methods of the anti-PD-1 sdAb in the present invention may refer to the patent application PCT/CN2019/071691.

A "full-length antibody" refers to an antibody having four full-length chains, including heavy chains and light chains containing Fc regions. The anti-CD47 antibody in the present invention refers to an antibody that can specifically bind to CD47, in particular, an antibody that can bind to human CD47. The anti-CD47 antibody in the present invention may be selected from the anti-CD47 antibody specifically described in PCT/CN2019/072929. The construction, expression, extraction, and purification methods of the anti-CD47 antibody in the present invention may refer to the patent application PCT/CN2019/072929.

A "mutation" is an alteration of one or more (several) amino acid residues at one or more (several) locations included in an antigen-binding protein or a protein fragment, that is, the substitution, insertion, and/or deletion of polypeptide. The substitution refers to substituting different amino acids for the amino acid occupying a certain location. The deletion refers to deleting the amino acid occupying a certain location. The insertion refers to refers to inserting 1 to 5 amino acids after the amino acid occupying a certain location.

The "amino acid sequence identity" is defined as the percentage of amino acid residues in a candidate sequence identical to the amino acid residues in a specific peptide or polypeptide sequence after the sequences are compared and gaps are introduced when necessary to obtain the maximum percent sequence identity without considering any conservative substitutions as part of the sequence identity. Sequence comparison can be performed in a variety of ways within the skill of the art to determine percent amino acid sequence identity, for example, publicly available computer software such as BLAST, BLAST-2, ALIGN or Megalign (DNASTAR) software is used. Those skilled in the art can determine appropriate parameters for measuring the comparison, including any algorithm required to obtain the maximum comparison over the full length of the compared sequences.

A "GS linker" refers to the GS combination of glycine (G) and serine (S), and is used to link a plurality of proteins together to form a fusion protein. The commonly used GS combination is (GGGGS)n, which changes the length of the linker sequence by changing n, and most of the GS combination is (GGGGS)3. In addition, glycine and serine may also produce different linker sequences through other combinations, for example, the GS combination of G15-linker used in the present invention is GGGGSGGGSGGGS.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 28, 2021, 168 KB, which is incorporated by reference herein.

DETAILED DESCRIPTION

Figure 1:
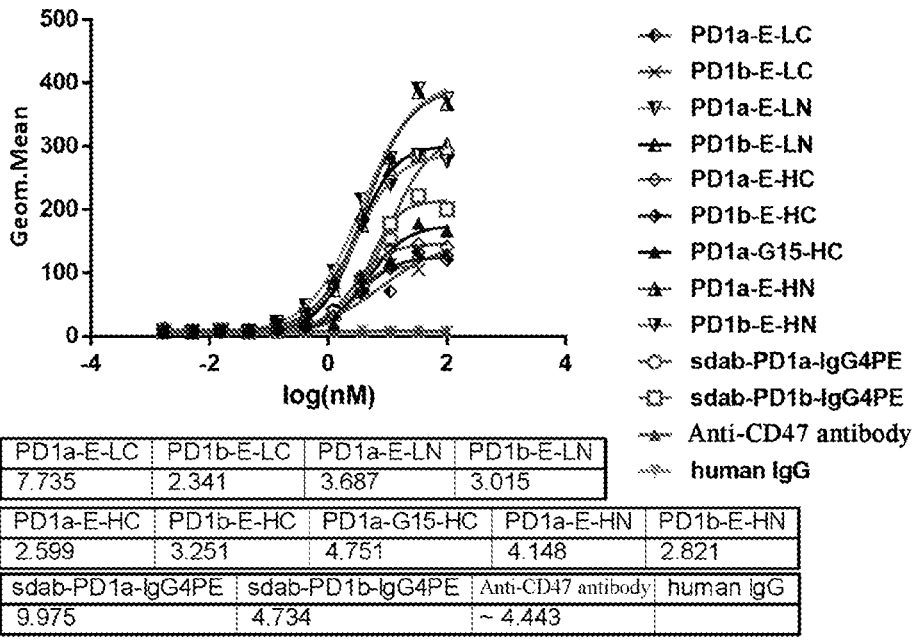
FIG. 1 shows the affinity between a sample and CHO-K1 cells expressing human PD-1 measured by a flow cytometer.

The present invention is described in detail below with reference to specific implementations. It should be understood that these implementations are merely intended to describe the present invention rather than to limit the scope of the present invention. In addition, it should be understood that, after reading the teaching of the present invention, those skilled in the art may make various changes or modifications to the present invention, and these equivalent forms also fall within the scope defined by the appended claims of this application. Unless otherwise specified, the methods and materials in the examples described below are commercially available and conventional products.

Example 1 Construction and Expression of Anti-CD47/anti-PD-1 Bispecific Antibody A series of anti-CD47/anti-PD-1 bispecific antibodies were designed by using an anti-CD47 monoclonal antibody (mAb) (the CDR, full-length nucleotide, and amino acid sequence of the antibody are shown in Table 1) and two PD-1 sdAbs (the CDR, full-length nucleotide, and amino acid sequence of the antibody are shown in Table 2). The PD-1 sdAb was fused to the N-terminus or C-terminus of the heavy chain or light chain of the anti-CD47 mAb by using two linker sequences (E-linker: EPKSSDKTHTSPPSP or G15-linker: GGGGSGGGGSGGGGS). Each bispecific antibody structure was composed of two identical fused polypeptide chains and two identical natural polypeptide chains, the DNA sequence expressing each polypeptide chain was inserted into the pTT5 vector between EcoRI and HindIII restriction sites. Each plasmid also includes a secretion signal sequence of a protein secreted into a growth medium. The PD-1 sdAb was fused to the N-terminus of IGg4-Fc with site mutation (S228P and L235E), as a control for biological activity measurement in vitro. The plasmids expressing the bispecific antibody protein are shown in Table 3.

TABLE 1

DNA and amino acid sequences of anti-CD47 mAbs

| | DNA sequence | SEQ ID NO: |
|---|---|---|
| Heavy chain DNA sequence of anti-CD47 antibody | GAGGTGCAGCTGGTGCAGTCCGGAGCTGAGGTGAAGAAG CCAGGATCCAGCGTGAAGGTGAGCTGCAAGGCTAGCGGC TACTCTTTCACCCACCATTGGATCCACTGGGTGAGGCAGG CTCCTGGACAGGGACTGGAGTGGATGGGCATGATCGACGC TTCCGATAGCGAGACAAGACTGTCTCAGAAGTTTAAGGAC CGCGTGACCATCACAGCCGATAAGTCTACCTCCACAGCTT ACATGGAGCTGTCTTCCCTGAGATCCGAGGACACCGCCGT GTACTATTGTGCTAGGCTGGGCCGGTACTATTTCGATTATTG GGGCCAGGGCACCACAGTGACAGTGAGCTCTGCCAGCAC AAAGGGCCCTTCCGTGTTCCCACTGGCTCCCTGCTCCAGA AGCACATCTGAGTCCACCGCCGCTCTGGGCTGTCTGGTGA AGGACTACTTCCCTGAGCCAGTGACCGTGTCCTGGAACAG CGGCGCCCTGACATCTGGCGTGCACACCTTTCCAGCTGTG CTGCAGTCCAGCGGCCTGTACTCCCTGTCTTCCGTGGTGA CAGTGCCCAGCTCTTCCCTGGGCACCAAGACATATACCTG CAACGTGGACCATAAGCCTTCCAATACCAAGGTGGATAAG AGGGTGGAGAGCAAGTACGGACCACCTTGCCCACCATGT CCAGCTCCTGAGTTTGAGGGAGGACCATCCGTGTTCCTGT TTCCTCCAAAGCCTAAGGACACCCTGATGATCAGCCGGAC ACCTGAGGTGACCTGCGTGGTGGTGGACGTGTCTCAGGA GGATCCAGAGGTGCAGTTCAACTGGTACGTGGATGGCGTG GAGGTGCACAATGCTAAGACCAAGCCAAGAGAGGAGCAG TTTAATTCCACATACCGCGTGGTGAGCGTGCTGACCGTGC TGCATCAGGATTGGCTGAACGGCAAGGAGTATAAGTGCAA GGTGTCCAATAAGGGCCTGCCCAGCTCTATCGAGAAGACA ATCAGCAAGGCTAAGGGACAGCCTAGGGAGCCACAGGTG TACACCCTGCCCCCTTCTCAGGAGGAGATGACAAAGAACC AGGTGTCCCTGACCTGTCTGGTGAAGGGCTTCTATCCAAG CGACATCGCTGTGGAGTGGGAGTCTAATGGCCAGCCCGAG AACAATTACAAGACCACACCACCCGTGCTGGACTCTGATG GCTCCTTCTTTCTGTATTCTAGGCTGACAGTGGATAAGTCC CGGTGGCAGGAGGGCAACGTGTTTAGCTGCTCTGTGATGC ACGAGGCCCTGCACAATCATTATACCCAGAAGTCCCTGAG CCTGTCTCTGGGCAAG | 3 |
| Heavy chain amino acid sequence H0 of anti-CD47 antibody | EVQLVQSGAEVKKPGSSVKVSCKASGYSFTHHWIHWVRQA PGQGLEWMGMIDASDSETRLSQKFKDRVTITADKSTSTAYM ELSSLRSEDTAVYYCARLGRYYFDYWGQGTTVTVSSASTKG PSVFPLAPCSRSTSESTAALGCLVKDYFPEPVTVSWNSGALTS GVHTFPAVLQSSGLYSLSSVVTVPSSSLGTKTYTCNVDHKPS NTKVDKRVESKYGPPCPPCPAPEFEGGPSVFLFPPKPKDTLMI SRTPEVTCVVVDVSQEDPEVQFNWYVDGVEVHNAKTKPRE EQFNSTYRVVSVLTVLHQDWLNGKEYKCKVSNKGLPSSIEK TISKAKGQPREPQVYTLPPSQEEMTKNQVSLTCLVKGFYPSD IAVEWESNGQPENNYKTTPPVLDSDGSFFLYSRLTVDKSRWQ EGNVFSCSVMHEALHNHYTQKSLSLSLGK | 4 |
| Light chain DNA sequence of anti-CD47 antibody | GAGATCGTGCTGACCCAGTCTCCAGCCACACTGTCTCTGT CCCCAGGAGAGAGGGCCACCCTGAGCTGCCGGGCTTCTG AGAACGTGGGCACATACATCTCCTGGTATCAGCAGAAGCC AGGACAGGCTCCTAGGCTGCTGATCTACGGCGCTAGCAAT AGATATACCGGCATCCCTGCTCGCTTCAGCGGATCTGGATC CGGCACAGACTTTACCCTGACAATCTCCAGCCTGGAGCCA | 5 |

TABLE 1-continued

DNA and amino acid sequences of anti-CD47 mAbs

| | | |
|---|---|---|
| | GAGGATTTCGCCGTGTACTATTGTGGCGAGTCCTACGGCC ACCTGTATACCTTTGGCGGCGGCACAAAGGTGGAGATCAA GCGAACGGTGGCTGCACCATCTGTCTTCATCTTCCCGCCAT CTGATGAGCAGTTGAAATCTGGAACTGCCTCTGTTGTGTG CCTGCTGAATAACTTCTATCCCAGAGAGGCCAAAGTACAG TGGAAGGTGGATAACGCCCTCCAATGGGTAACTCCCAGG AGAGTGTCACAGAGCAGGACAGCAAGGACAGCACCTACA GCCTCAGCAGCACCCTGACGCTGAGCAAAGCAGACTACG AGAAACACAAAGTCTACGCCTGCGAAGTCACCCATCAGG GCCTGAGCTCGCCCGTCACAAAGAGCTTCAACAGGGGAG AGTGT | |
| Light chain amino acid sequence L0 of anti-CD47 antibody | EIVLTQSPATLSLSPGERATLSCRASENVGTYISWYQQKPGQA PRLLIYGASNRYTGIPARFSGSGSGTDFTLTISSLEPEDFAVYY CGESYGHLYTFGGGTKVEIKRTVAAPSVFIFPPSDEQLKSGTA SVVCLLNNFYPREAKVQWKVDNALQSGNSQESVTEQDSKD STYSLSSTLTLSKADYEKHKVYACEVTHQGLSSPVTKSFNRG EC | 6 |

| | CDR1 sequence | SEQ ID NO: | CDR2 sequence | SEQ ID NO: | CDR3 sequence | SEQ ID NO: |
|---|---|---|---|---|---|---|
| Heavy chain CDR sequence of anti-CD47 antibody | GYSFTHHWI H | 33 | MIDASDSET RLSQKFKD | 34 | LGRYYFDY | 35 |
| Light chain CDR sequence of anti-CD47 antibody | RASENVGT YIS | 36 | GASNRYT | 37 | GESYGHLYT | 38 |

TABLE 2

DNA and amino acid sequences of PD-1 sdAb

| | Sequence | SEQ ID NO: |
|---|---|---|
| DNA sequence of PD-1a sdAb | GAAGTGCAGCTGGTGGAATCTGGCGGCGGACTGGTGCAG CCTGGCGGCTCTCTGCGGCTGTCTTGTGCCGTGTCCGGCA ACATCTACAACCGGAACTTCATGGGCTGGTTCCGGCAGGC CCCCGGAAAAGGCCGCGAAGGCGTGTCCGCCATCTACAC GGGCACCTCCAGAACATATTACGCCGACAGCGTGAAAGG TAGATTCACCATCTCCAGAGACAACGCCAAGAACACCGT GTACCTGCAGATGAACTCCCTGAGACCAGAGGACACAGC TGTGTACTATTGCGCTGCTGATCTGAGGGATGGCTTCTGG GACACCGGCGTGTGGAACACCTGGGGCCAGGGCACACTG GTCACTGTGTCTTCC | 29 |
| Amino acid sequence of PD-1a sdAb | EVQLVESGGGLVQPGGSLRLSCAVSGNIYNRNFMGWFRQAP GKGREGVSAIYTGTSRTYYADSVKGRFTISRDNAKNTVYLQ MNSLRPEDTAVYYCAADLRDGFWDTGVWNTWGQGTLVTV SS | 30 |
| DNA sequence of PD-1b sdAb | GAGGTGCAGCTGGTCGAGTCTGGCGGTGGCCTGGTTCAG CCCGGCGGCTCCCTGCGGCTGAGCTGCGCCGTGTCCGGC AACATCTACAACAGAAACTTCATGGGCTGGTTTAGACAGG CTCCTGGCAAGGGACTGGAAGGCGTGTCCGCCATCTACA CCGGCACCTCTCGGACTTACTACGCCGACTCTGTCAAGGG CAGATTCACCATCTCCCGGGACAACTCCAAGAACACAGT GTATCTGCAGATGAACAGCCTGAG AGCCGAGGATACCGCTGTGTACTACTGCGCTGCTGATCTG AGAGAGGGCTTCTGGGACACCGGCGTGTGGAATACCTGG GGCCAGGGCACCCTGGTGACCGTGTCTTCT | 31 |
| Amino acid sequence of PD-1b sdAb | EVQLVESGGGLVQPGGSLRLSCAVSGNIYNRNFMGWFRQAP GKGLEGVSAIYTGTSRTYYADSVKGRFTISRDNSKNTVYLQ MNSLRAEDTAVYYCAADLREGFWDTGVWNTWGQGTLVTV SS | 32 |

TABLE 2-continued

DNA and amino acid sequences of PD-1 sdAb

| | CDR1 sequence | SEQ ID NO: | CDR2 sequence | SEQ ID NO: | CDR3 sequence | SEQ ID NO: |
|---|---|---|---|---|---|---|
| CDR amino acid sequence of PD-1a sdAb | GNIYNRNFMG | 39 | AIYTGTSRTYYADSVKG | 40 | DLRDGFWDTGVWNT | 41 |
| CDR amino acid sequence of PD-1b sdAb | GNIYNRNFMG | 42 | AIYTGTSRTYYADSVKG | 43 | DLREGFWDTGVWNT | 44 |

After the expression plasmids were transfected into CHO-3E7 host cells, the resulting host cells were cultured in an incubator at 37° C. and 100 rpm for 6 days. The supernatant was extracted by centrifugation, and a bispecific antibody protein was purified with a Protein A column.

As described above, the anti-CD47 mAb was composed of the heavy chain H0 and the light chain L0. The PD-1 sdAb was fused to the N-terminus or C-terminus of the heavy chain or light chain of the anti-CD47 mAb by two linker sequences (E-linker: EPKSSDKTHTSPPSP or G15-linker: GGGGSGGGGSGGGGS) to produce a series of different bispecific antibodies. First, the E-linker sequence was used to construct the following fusion proteins: (1). the two sdAbs PD1a and PD1b were respectively fused to the C-terminus of the heavy chain H0 to produce new polypeptides respectively referred to as H1 and H2; (2). the two sdAbs PD1a and PD1b were respectively fused to the N-terminus of the heavy chain H0 to produce new polypeptides respectively referred to as H3 and H4; (3). the two sdAbs PD1a and PD1b were respectively fused to the C-terminus of the light chain L0 to produce new polypeptides respectively referred to as L1 and L2; and (4). the two sdAbs PD1a and PD1b were respectively fused to the N-terminus of the light chain L0 to produce new polypeptides respectively referred to as L3 and L4. Similarly, the G15-linker sequence was then used to construct the following fusion proteins: the PD1a sdAb was fused to the C-terminus of the heavy chain H0 to produce a new polypeptide referred to as H5.

These constructed heavy chain fusion proteins H1, H2, H3, H4, and H5 were separately combined with the unmodified parental light chain polypeptide chain L0, or these constructed light chain fusion proteins L1, L2, L3, and L4 were separately combined with the unmodified heavy chain polypeptide chain H0, to produce a series of bispecific antibodies. The heavy chain fusion protein H1 was combined with the parental light chain L0 to produce a bispecific antibody PD1a-E-HC. The heavy chain fusion protein H2 was combined with the parental light chain L0 to produce a bispecific antibody PD1b-E-HC. The heavy chain fusion protein H3 was combined with the parental light chain L0 to produce a bispecific antibody PD1a-E-HN. The heavy chain fusion protein H4 was combined with the parental light chain L0 to produce a bispecific antibody PD1b-E-HN. The heavy chain fusion protein H5 was combined with the parental light chain L0 to produce a bispecific antibody PD1a-G15-HC. The light chain fusion protein L1 was combined with the parental heavy chain H0 to produce a bispecific antibody PD1a-E-LC. The light chain fusion protein L2 was combined with the parental heavy chain H0 to produce a bispecific antibody PD1b-E-LC. The light chain fusion protein L3 was combined with the parental heavy chain H0 to produce a bispecific antibody PD1a-E-LN. The light chain fusion protein L4 was combined with the parental heavy chain H0 to produce a bispecific antibody PD1b-E-LN.

The human IGg4-Fc was modified by site mutation (S228P and L235E), and then the two sdAbs PD1a and PD1b were respectively linked to the N-terminus of the human IGg4-Fc, to produce new fusion proteins H6 and H7, to further construct the Fc fusion proteins sdAb-PD1a-IgG4PE and sdAb-PD1b-IgG4PE.

TABLE 3

Plasmids and proteins for construction of bispecific antibody

| Protein | Component | Plasmid | Amino acid SEQ ID NO: |
|---|---|---|---|
| CD47 | H0 | pTT5-CD47HC | 4 |
| | L0 | pTT5-CD47LC | 6 |
| PD1a-E-HC | H1 | pTT5-CD47HC-E-PD1a | 8 |
| | L0 | pTT5-CD47LC | 6 |
| PD1b-E-HC | H2 | pTT5-CD47HC-E-PD1b | 10 |
| | L0 | pTT5-CD47LC | 6 |
| PD1a-E-HN | H3 | pTT5-PD1a-E-CD47HC | 12 |
| | L0 | pTT5-CD47LC | 6 |
| PD1b-E-HN | H4 | pTT5-PD1b-E-CD47HC | 14 |
| | L0 | pTT5-CD47LC | 6 |
| PD1a-E-LC | L1 | pTT5-CD47LC-E-PD1a | 16 |
| | H0 | pTT5-CD47HC | 4 |
| PD1b-E-LC | L2 | pTT5-CD47LC-E-PD1b | 18 |
| | H0 | pTT5-CD47HC | 4 |
| PD1a-E-LN | L3 | pTT5-PD1a-E-CD47LC | 20 |
| | H0 | pTT5-CD47HC | 4 |
| PD1b-E-LN | L4 | pTT5-PD1b-E-CD47LC | 22 |
| | H0 | pTT5-CD47HC | 4 |
| PD1a-G15-HC | H5 | pTT5-CD47HC-G15-PD1a | 24 |
| | L0 | pTT5-CD47LC | 6 |
| sdAb-PD1a-IgG4PE | H6 | pTT5-sdAb-PD1a-IgG4PE | 26 |
| sdAb-PD1b-IgG4PE | H7 | pTT5-sdAb-PD1b-IgG4PE | 28 |

DNA sequence of secretion signal peptide
(SEQ ID NO: 1)
ATGGGCTGGTCCTGCATCATCCTGTTCCTGGTGGCTACCGCCACCGGCGTGCA

CTCC

Amino acid sequence of secretion signal peptide
(SEQ ID NO: 2)
MGWSCIILFLVATATGVHS DNA sequence of polypeptide chain H0
(SEQ ID NO: 3)
GAGGTGCAGCTGGTGCAGTCCGGAGCTGAGGTGAAGAAGCCAGGATCCAGCGTG

AAGGTGAGCTGCAAGGCTAGCGGCTACTCTTTCACCCACCATTGGATCCACTGGG

TGAGGCAGGCTCCTGGACAGGGACTGGAGTGGATGGGCATGATCGACGCTTCCGA

TAGCGAGACAAGACTGTCTCAGAAGTTTAAGGACCGCGTGACCATCACAGCCGAT

AAGTCTACCTCCACAGCTTACATGGAGCTGTCTTCCCTGAGATCCGAGGACACCG

CCGTGTACTATTGTGCTAGGCTGGGCCGGTACTATTTCGATTATTGGGGCCAGGGC

ACCACAGTGACAGTGAGCTCTGCCAGCACAAAGGGCCCTTCCGTGTTCCCACTGG

CTCCCTGCTCCAGAAGCACATCTGAGTCCACCGCCGCTCTGGGCTGTCTGGTGAA

GGACTACTTCCCTGAGCCAGTGACCGTGTCCTGGAACAGCGGCGCCCTGACATCT

GGCGTGCACACCTTTCCAGCTGTGCTGCAGTCCAGCGGCCTGTACTCCCTGTCTTC

CGTGGTGACAGTGCCCAGCTCTTCCCTGGGCACCAAGACATATACCTGCAACGTG

GACCATAAGCCTTCCAATACCAAGGTGGATAAGAGGGTGGAGAGCAAGTACGGAC

CACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAG

Amino acid sequence of polypeptide chain H0
(SEQ ID NO: 4)
EVQLVQSGAEVKKPGSSVKVSCKASGYSFTHHWIHWVRQAPGQGLEWMGMIDASD

SETRLSQKFKDRVTITADKSTSTAYMELSSLRSEDTAVYYCARLGRYYFDYWGQGTT

VTVSSASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPPCPA

PEFEGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

DNA sequence of polypeptide chain L0
(SEQ ID NO: 5)
GAGATCGTGCTGACCCAGTCTCCAGCCACACTGTCTCTGTCCCCAGGAGAGAGGG

CCACCCTGAGCTGCCGGGCTTCTGAGAACGTGGGCACATACATCTCCTGGTATCA

GCAGAAGCCAGGACAGGCTCCTAGGCTGCTGATCTACGGCGCTAGCAATAGATAT

ACCGGCATCCCTGCTCGCTTCAGCGGATCTGGATCCGGCACAGACTTTACCCTGAC

AATCTCCAGCCTGGAGCCAGAGGATTTCGCCGTGTACTATTGTGGCGAGTCCTACG

GCCACCTGTATACCTTTGGCGGCGGCACAAAGGTGGAGATCAAGCGAACGGTGGC

TGCACCATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAG

GACAGCAAGGACAGCACCTACAGCCTCAGCAGCACCCTGACGCTGAGCAAAGCA

GACTACGAGAAACACAAAGTCTACGCCTGCGAAGTCACCCATCAGGGCCTGAGC

TCGCCCGTCACAAAGAGCTTCAACAGGGGAGAGTGT

Amino acid sequence of polypeptide chain L0
(SEQ ID NO: 6)
EIVLTQSPATLSLSPGERATLSCRASENVGTYISWYQQKPGQAPRLLIYGASNRYTGIP

ARFSGSGSGTDFTLTISSLEPEDFAVYYCGESYGHLYTFGGGTKVEIKRTVAAPSVFIFP

PSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

DNA sequence of polypeptide chain H1
(SEQ ID NO: 7)
GAGGTGCAGCTGGTGCAGTCCGGAGCTGAGGTGAAGAAGCCAGGATCCAGCGTG

AAGGTGAGCTGCAAGGCTAGCGGCTACTCTTTCACCCACCATTGGATCCACTGGG

TGAGGCAGGCTCCTGGACAGGGACTGGAGTGGATGGGCATGATCGACGCTTCCGA

TAGCGAGACAAGACTGTCTCAGAAGTTTAAGGACCGCGTGACCATCACAGCCGAT

AAGTCTACCTCCACAGCTTACATGGAGCTGTCTTCCCTGAGATCCGAGGACACCG

CCGTGTACTATTGTGCTAGGCTGGGCCGGTACTATTTCGATTATTGGGGCCAGGGC

ACCACAGTGACAGTGAGCTCTGCCAGCACAAAGGGCCCTTCCGTGTTCCCACTGG

CTCCCTGCTCCAGAAGCACATCTGAGTCCACCGCCGCTCTGGGCTGTCTGGTGAA

GGACTACTTCCCTGAGCCAGTGACCGTGTCCTGGAACAGCGGCGCCCTGACATCT

GGCGTGCACACCTTTCCAGCTGTGCTGCAGTCCAGCGGCCTGTACTCCCTGTCTTC

CGTGGTGACAGTGCCCAGCTCTTCCCTGGGCACCAAGACATATACCTGCAACGTG

GACCATAAGCCTTCCAATACCAAGGTGGATAAGAGGGTGGAGAGCAAGTACGGAC

CACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

-continued

```
GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAGGAACCTAAGTCTAGCGACAAAACTCATACCAGCCCCCCTAGTCC

AGAAGTGCAGCTGGTGGAATCTGGCGGCGGACTGGTGCAGCCTGGCGGCTCTCT

GCGGCTGTCTTGTGCCGTGTCCGGCAACATCTACAACCGGAACTTCATGGGCTGG

TTCCGGCAGGCCCCCGGAAAAGGCCGCGAAGGCGTGTCCGCCATCTACACGGGC

ACCTCCAGAACATATTACGCCGACAGCGTGAAAGGTAGATTCACCATCTCCAGAG

ACAACGCCAAGAACACCGTGTACCTGCAGATGAACTCCCTGAGACCAGAGGACA

CAGCTGTGTACTATTGCGCTGCTGATCTGAGGGATGGCTTCTGGGACACCGGCGTG

TGGAACACCTGGGGCCAGGGCACACTGGTCACTGTGTCTTCC
```

Amino acid sequence of polypeptide chain H1
(SEQ ID NO: 8)

```
EVQLVQSGAEVKKPGSSVKVSCKASGYSFTHHWIHWVRQAPGQGLEWMGMIDASD

SETRLSQKFKDRVTITADKSTSTAYMELSSLRSEDTAVYYCARLGRYYFDYWGQTT

VTVSSASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPPCPA

PEFEGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKEPKSSDKTHTSPP

SPEVQLVESGGGLVQPGGSLRLSCAVSGNIYNRNFMGWFRQAPGKGREGVSAIYTGT

SRTYYADSVKGRFTISRDNAKNTVYLQMNSLRPEDTAVYYCAADLRDGFWDTGVW

NTWGQGTLVTVSS
```

DNA sequence of polypeptide chain H2
(SEQ ID NO: 9)

```
GAGGTGCAGCTGGTGCAGTCCGGAGCTGAGGTGAAGAAGCCAGGATCCAGCGTG

AAGGTGAGCTGCAAGGCTAGCGGCTACTCTTTCACCCACCATTGGATCCACTGGG

TGAGGCAGGCTCCTGGACAGGGACTGGAGTGGATGGGCATGATCGACGCTTCCGA

TAGCGAGACAAGACTGTCTCAGAAGTTTAAGGACCGCGTGACCATCACAGCCGAT

AAGTCTACCTCCACAGCTTACATGGAGCTGTCTTCCCTGAGATCCGAGGACACCG

CCGTGTACTATTGTGCTAGGCTGGGCCGGTACTATTTCGATTATTGGGGCCAGGGC

ACCACAGTGACAGTGAGCTCTGCCAGCACAAAGGGCCCTTCCGTGTTCCCACTGG

CTCCCTGCTCCAGAAGCACATCTGAGTCCACCGCCGCTCTGGGCTGTCTGGTGAA

GGACTACTTCCCTGAGCCAGTGACCGTGTCCTGGAACAGCGGCGCCCTGACATCT

GGCGTGCACACCTTTCCAGCTGTGCTGCAGTCCAGCGGCCTGTACTCCCTGTCTTC

CGTGGTGACAGTGCCCAGCTCTTCCCTGGGCACCAAGACATATACCTGCAACGTG

GACCATAAGCCTTCCAATACCAAGGTGGATAAGAGGGTGGAGAGCAAGTACGGAC

CACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA
```

-continued

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAGGAACCTAAGTCTAGCGACAAAACTCATACCAGCCCCCCTAGTCC

AGAGGTGCAGCTGGTCGAGTCTGGCGGTGGCCTGGTTCAGCCCGGCGGCTCCCTG

CGGCTGAGCTGCGCCGTGTCCGGCAACATCTACAACAGAAACTTCATGGGCTGGT

TTAGACAGGCTCCTGGCAAGGGACTGGAAGGCGTGTCCGCCATCTACACCGGCAC

CTCTCGGACTTACTACGCCGACTCTGTCAAGGGCAGATTCACCATCTCCCGGGAC

AACTCCAAGAACACAGTGTATCTGCAGATGAACAGCCTGAGAGCCGAGGATACCG

CTGTGTACTACTGCGCTGCTGATCTGAGAGAGGGCTTCTGGGACACCGGCGTGTG

GAATACCTGGGGCCAGGGCACCCTGGTGACCGTGTCTTCT

Amino acid sequence of polypeptide chain H2
(SEQ ID NO: 10)
EVQLVQSGAEVKKPGSSVKVSCKASGYSFTHHWIHWVRQAPGQGLEWMGMIDASD

SETRLSQKFKDRVTITADKSTSTAYMELSSLRSEDTAVYYCARLGRYYFDYWGQTT

VTVSSASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPPCPA

PEFEGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKEPKSSDKTHTSPP

SPEVQLVESGGGLVQPGGSLRLSCAVSGNIYNRNFMGWFRQAPGKGLEGVSAIYTGT

SRTYYADSVKGRFTISRDNSKNTVYLQMNSLRAEDTAVYYCAADLREGFWDTGVW

NTWGQGTLVTVSS

DNA sequence of polypeptide chain H3
(SEQ ID NO: 11)
GAAGTGCAGCTGGTGGAATCTGGCGGCGGACTGGTGCAGCCTGGCGGCTCTCTGC

GGCTGTCTTGTGCCGTGTCCGGCAACATCTACAACCGGAACTTCATGGGCTGGTTC

CGGCAGGCCCCCGGAAAAGGCCGCGAAGGCGTGTCCGCCATCTACACGGGCACC

TCCAGAACATATTACGCCGACAGCGTGAAAGGTAGATTCACCATCTCCAGAGACA

ACGCCAAGAACACCGTGTACCTGCAGATGAACTCCCTGAGACCAGAGGACACAG

CTGTGTACTATTGCGCTGCTGATCTGAGGGATGGCTTCTGGGACACCGGCGTGTGG

AACACCTGGGGCCAGGGCACACTGGTCACTGTGTCTTCCGAACCTAAGTCTAGCG

ACAAAACTCATACCAGCCCCCCTAGTCCAGAGGTGCAGCTGGTGCAGTCCGGAGC

TGAGGTGAAGAAGCCAGGATCCAGCGTGAAGGTGAGCTGCAAGGCTAGCGGCTA

CTCTTTCACCCACCATTGGATCCACTGGGTGAGGCAGGCTCCTGGACAGGGACTG

GAGTGGATGGGCATGATCGACGCTTCCGATAGCGAGACAAGACTGTCTCAGAAGT

TTAAGGACCGCGTGACCATCACAGCCGATAAGTCTACCTCCACAGCTTACATGGA

```
-continued
GCTGTCTTCCCTGAGATCCGAGGACACCGCCGTGTACTATTGTGCTAGGCTGGGCC

GGTACTATTTCGATTATTGGGGCCAGGGCACCACAGTGACAGTGAGCTCTGCCAG

CACAAAGGGCCCTTCCGTGTTCCCACTGGCTCCCTGCTCCAGAAGCACATCTGAG

TCCACCGCCGCTCTGGGCTGTCTGGTGAAGGACTACTTCCCTGAGCCAGTGACCG

TGTCCTGGAACAGCGGCGCCCTGACATCTGGCGTGCACACCTTTCCAGCTGTGCT

GCAGTCCAGCGGCCTGTACTCCCTGTCTTCCGTGGTGACAGTGCCCAGCTCTTCC

TGGGCACCAAGACATATACCTGCAACGTGGACCATAAGCCTTCCAATACCAAGGT

GGATAAGAGGGTGGAGAGCAAGTACGGACCACCTTGCCCACCATGTCCAGCTCCT

GAGTTTGAGGGAGGACCATCCGTGTTCCTGTTTCCTCCAAAGCCTAAGGACACCC

TGATGATCAGCCGGACACCTGAGGTGACCTGCGTGGTGGTGGACGTGTCTCAGGA

GGATCCAGAGGTGCAGTTCAACTGGTACGTGGATGGCGTGGAGGTGCACAATGCT

AAGACCAAGCCAAGAGAGGAGCAGTTTAATTCCACATACCGCGTGGTGAGCGTG

CTGACCGTGCTGCATCAGGATTGGCTGAACGGCAAGGAGTATAAGTGCAAGGTGT

CCAATAAGGGCCTGCCCAGCTCTATCGAGAAGACAATCAGCAAGGCTAAGGGACA

GCCTAGGGAGCCACAGGTGTACACCCTGCCCCCTTCTCAGGAGGAGATGACAAA

GAACCAGGTGTCCCTGACCTGTCTGGTGAAGGGCTTCTATCCAAGCGACATCGCT

GTGGAGTGGGAGTCTAATGGCCAGCCCGAGAACAATTACAAGACCACACCACCC

GTGCTGGACTCTGATGGCTCCTTCTTTCTGTATTCTAGGCTGACAGTGGATAAGTC

CCGGTGGCAGGAGGGCAACGTGTTTAGCTGCTCTGTGATGCACGAGGCCCTGCAC

AATCATTATACCCAGAAGTCCCTGAGCCTGTCTCTGGGCAAG

Amino acid sequence of polypeptide chain H3
                                                    (SEQ ID NO: 12)
EVQLVESGGGLVQPGGSLRLSCAVSGNIYNRNFMGWFRQAPGKGREGVSAIYTGTSR

TYYADSVKGRFTISRDNAKNTVYLQMNSLRPEDTAVYYCAADLRDGFWDTGVWNT

WGQGTLVTVSSEPKSSDKTHTSPPSPEVQLVQSGAEVKKPGSSVKVSCKASGYSFTH

HWIHWVRQAPGQGLEWMGMIDASDSETRLSQKFKDRVTITADKSTSTAYMELSSLR

SEDTAVYYCARLGRYYFDYWGQGTTVTVSSASTKGPSVFPLAPCSRSTSESTAALGC

LVKDYFPEPVTVSWNSGALTSGVHTFPAVLQSSGLYSLSSVVTVPSSSLGTKTYTCNV

DHKPSNTKVDKRVESKYGPPCPPCPAPEFEGGPSVFLFPPKPKDTLMISRTPEVTCVVV

DVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIA

VEWESNGQPENNYKTTPPVLDSDGSFFLYSRLTVDKSRWQEGNVFSCSVMHEALHN

HYTQKSLSLSLGK

DNA sequence of polypeptide chain H4
                                                    (SEQ ID NO: 13)
GAGGTGCAGCTGGTCGAGTCTGGCGGTGGCCTGGTTCAGCCCGGCGGCTCCCTGC

GGCTGAGCTGCGCCGTGTCCGGCAACATCTACAACAGAAACTTCATGGGCTGGTT

TAGACAGGCTCCTGGCAAGGGACTGGAAGGCGTGTCCGCCATCTACACCGGCACC

TCTCGGACTTACTACGCCGACTCTGTCAAGGGCAGATTCACCATCTCCCGGGACA

ACTCCAAGAACACAGTGTATCTGCAGATGAACAGCCTGAGAGCCGAGGATACCGC

TGTGTACTACTGCGCTGCTGATCTGAGAGAGGGCTTCTGGGACACCGGCGTGTGG

AATACCTGGGGCCAGGGCACCCTGGTGACCGTGTCTTCTGAACCTAAGTCTAGCG

ACAAAACTCATACCAGCCCCCCTAGTCCAGAGGTGCAGCTGGTGCAGTCCGGAGC
```

```
TGAGGTGAAGAAGCCAGGATCCAGCGTGAAGGTGAGCTGCAAGGCTAGCGGCTA

CTCTTTCACCCACCATTGGATCCACTGGGTGAGGCAGGCTCCTGGACAGGGACTG

GAGTGGATGGGCATGATCGACGCTTCCGATAGCGAGACAAGACTGTCTCAGAAGT

TTAAGGACCGCGTGACCATCACAGCCGATAAGTCTACCTCCACAGCTTACATGGA

GCTGTCTTCCCTGAGATCCGAGGACACCGCCGTGTACTATTGTGCTAGGCTGGGCC

GGTACTATTTCGATTATTGGGGCCAGGGCACCACAGTGACAGTGAGCTCTGCCAG

CACAAAGGGCCCTTCCGTGTTCCCACTGGCTCCCTGCTCCAGAAGCACATCTGAG

TCCACCGCCGCTCTGGGCTGTCTGGTGAAGGACTACTTCCCTGAGCCAGTGACCG

TGTCCTGGAACAGCGGCGCCCTGACATCTGGCGTGCACACCTTTCCAGCTGTGCT

GCAGTCCAGCGGCCTGTACTCCCTGTCTTCCGTGGTGACAGTGCCCAGCTCTTCCC

TGGGCACCAAGACATATACCTGCAACGTGGACCATAAGCCTTCCAATACCAAGGT

GGATAAGAGGGTGGAGAGCAAGTACGGACCACCTTGCCCACCATGTCCAGCTCCT

GAGTTTGAGGGAGGACCATCCGTGTTCCTGTTTCCTCCAAAGCCTAAGGACACCC

TGATGATCAGCCGGACACCTGAGGTGACCTGCGTGGTGGTGGACGTGTCTCAGGA

GGATCCAGAGGTGCAGTTCAACTGGTACGTGGATGGCGTGGAGGTGCACAATGCT

AAGACCAAGCCAAGAGAGGAGCAGTTTAATTCCACATACCGCGTGGTGAGCGTG

CTGACCGTGCTGCATCAGGATTGGCTGAACGGCAAGGAGTATAAGTGCAAGGTGT

CCAATAAGGGCCTGCCCAGCTCTATCGAGAAGACAATCAGCAAGGCTAAGGGACA

GCCTAGGGAGCCACAGGTGTACACCCTGCCCCCTTCTCAGGAGGAGATGACAAA

GAACCAGGTGTCCCTGACCTGTCTGGTGAAGGGCTTCTATCCAAGCGACATCGCT

GTGGAGTGGGAGTCTAATGGCCAGCCCGAGAACAATTACAAGACCACACCACCC

GTGCTGGACTCTGATGGCTCCTTCTTTCTGTATTCTAGGCTGACAGTGGATAAGTC

CCGGTGGCAGGAGGGCAACGTGTTTAGCTGCTCTGTGATGCACGAGGCCCTGCAC

AATCATTATACCCAGAAGTCCCTGAGCCTGTCTCTGGGCAAG
```

Amino acid sequence of polypeptide chain H4
(SEQ ID NO: 14)

```
EVQLVESGGGLVQPGGSLRLSCAVSGNIYNRNFMGWFRQAPGKGLEGVSAIYTGTSR

TYYADSVKGRFTISRDNSKNTVYLQMNSLRAEDTAVYYCAADLREGFWDTGVWNT

WGQGTLVTVSSEPKSSDKTHTSPPSPEVQLVQSGAEVKKPGSSVKVSCKASGYSFTH

HWIHWVRQAPGQGLEWMGMIDASDSETRLSQKFKDRVTITADKSTSTAYMELSSLR

SEDTAVYYCARLGRYYFDYWGQGTTVTVSSASTKGPSVFPLAPCSRSTSESTAALGC

LVKDYFPEPVTVSWNSGALTSGVHTFPAVLQSSGLYSLSSVVTVPSSSLGTKTYTCNV

DHKPSNTKVDKRVESKYGPPCPPCPAPEFEGGPSVFLFPPKPKDTLMISRTPEVTCVVV

DVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIA

VEWESNGQPENNYKTTPPVLDSDGSFFLYSRLTVDKSRWQEGNVFSCSVMHEALHN

HYTQKSLSLSLGK
```

DNA sequence of polypeptide chain L1
(SEQ ID NO: 15)

```
GAGATCGTGCTGACCCAGTCTCCAGCCACACTGTCTCTGTCCCCAGGAGAGAGGG

CCACCCTGAGCTGCCGGGCTTCTGAGAACGTGGGCACATACATCTCCTGGTATCA

GCAGAAGCCAGGACAGGCTCCTAGGCTGCTGATCTACGGCGCTAGCAATAGATAT
```

-continued
ACCGGCATCCCTGCTCGCTTCAGCGGATCTGGATCCGGCACAGACTTTACCCTGAC

AATCTCCAGCCTGGAGCCAGAGGATTTCGCCGTGTACTATTGTGGCGAGTCCTACG

GCCACCTGTATACCTTTGGCGGCGGCACAAAGGTGGAGATCAAGCGAACGGTGGC

TGCACCATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAG

GACAGCAAGGACAGCACCTACAGCCTCAGCAGCACCCTGACGCTGAGCAAAGCA

GACTACGAGAAACACAAAGTCTACGCCTGCGAAGTCACCCATCAGGGCCTGAGC

TCGCCCGTCACAAAGAGCTTCAACAGGGGAGAGTGTGAACCTAAGTCTAGCGAC

AAAACTCATACCAGCCCCCCTAGTCCAGAAGTGCAGCTGGTGGAATCTGGCGGCG

GACTGGTGCAGCCTGGCGGCTCTCTGCGGCTGTCTTGTGCCGTGTCCGGCAACAT

CTACAACCGGAACTTCATGGGCTGGTTCCGGCAGGCCCCCGGAAAAGGCCGCGA

AGGCGTGTCCGCCATCTACACGGGCACCTCCAGAACATATTACGCCGACAGCGTG

AAAGGTAGATTCACCATCTCCAGAGACAACGCCAAGAACACCGTGTACCTGCAGA

TGAACTCCCTGAGACCAGAGGACACAGCTGTGTACTATTGCGCTGCTGATCTGAG

GGATGGCTTCTGGGACACCGGCGTGTGGAACACCTGGGGCCAGGGCACACTGGT

CACTGTGTCTTCC

Amino acid sequence of polypeptide chain L1
(SEQ ID NO: 16)
EIVLTQSPATLSLSPGERATLSCRASENVGTYISWYQQKPGQAPRLLIYGASNRYTGIP

ARFSGSGSGTDFTLTISSLEPEDFAVYYCGESYGHLYTFGGGTKVEIKRTVAAPSVFIFP

PSDEQLKSGTASVVCLLNNFYPREAKVQWKVDNALQSGNSQESVTEQDSKDSTYSL

SSTLTLSKADYEKHKVYACEVTHQGLSSPVTKSFNRGECEPKSSDKTHTSPPSPEVQL

VESGGGLVQPGGSLRLSCAVSGNIYNRNFMGWFRQAPGKGREGVSAIYTGTSRTYYA

DSVKGRFTISRDNAKNTVYLQMNSLRPEDTAVYYCAADLRDGFWDTGVWNTWGQ

GTLVTVSS

DNA sequence of polypeptide chain L2
(SEQ ID NO: 17)
GAGATCGTGCTGACCCAGTCTCCAGCCACACTGTCTCTGTCCCCAGGAGAGAGGG

CCACCCTGAGCTGCCGGGCTTCTGAGAACGTGGGCACATACATCTCCTGGTATCA

GCAGAAGCCAGGACAGGCTCCTAGGCTGCTGATCTACGGCGCTAGCAATAGATAT

ACCGGCATCCCTGCTCGCTTCAGCGGATCTGGATCCGGCACAGACTTTACCCTGAC

AATCTCCAGCCTGGAGCCAGAGGATTTCGCCGTGTACTATTGTGGCGAGTCCTACG

GCCACCTGTATACCTTTGGCGGCGGCACAAAGGTGGAGATCAAGCGAACGGTGGC

TGCACCATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAG

GACAGCAAGGACAGCACCTACAGCCTCAGCAGCACCCTGACGCTGAGCAAAGCA

GACTACGAGAAACACAAAGTCTACGCCTGCGAAGTCACCCATCAGGGCCTGAGC

TCGCCCGTCACAAAGAGCTTCAACAGGGGAGAGTGTGAACCTAAGTCTAGCGAC

AAAACTCATACCAGCCCCCCTAGTCCAGAGGTGCAGCTGGTCGAGTCTGGCGGTG

GCCTGGTTCAGCCCGGCGGCTCCCTGCGGCTGAGCTGCGCCGTGTCCGGCAACAT

CTACAACAGAAACTTCATGGGCTGGTTTAGACAGGCTCCTGGCAAGGGACTGGAA

-continued

```
GGCGTGTCCGCCATCTACACCGGCACCTCTCGGACTTACTACGCCGACTCTGTCAA

GGGCAGATTCACCATCTCCCGGGACAACTCCAAGAACACAGTGTATCTGCAGATG

AACAGCCTGAGAGCCGAGGATACCGCTGTGTACTACTGCGCTGCTGATCTGAGAG

AGGGCTTCTGGGACACCGGCGTGTGGAATACCTGGGGCCAGGGCACCCTGGTGA

CCGTGTCTTCT
```

Amino acid sequence of polypeptide chain L2
(SEQ ID NO: 18)

```
EIVLTQSPATLSLSPGERATLSCRASENVGTYISWYQQKPGQAPRLLIYGASNRYTGIP

ARFSGSGSGTDFTLTISSLEPEDFAVYYCGESYGHLYTFGGGTKVEIKRTVAAPSVFIFP

PSDEQLKSGTASVVCLLNNFYPREAKVQWKVDNALQSGNSQESVTEQDSKDSTYSL

SSTLTLSKADYEKHKVYACEVTHQGLSSPVTKSFNRGECEPKSSDKTHTSPPSPEVQL

VESGGGLVQPGGSLRLSCAVSGNIYNRNFMGWFRQAPGKGLEGVSAIYTGTSRTYYA

DSVKGRFTISRDNSKNTVYLQMNSLRAEDTAVYYCAADLREGFWDTGVWNTWGQG

TLVTVSS
```

DNA sequence of polypeptide chain L3
(SEQ ID NO: 19)

```
GAAGTGCAGCTGGTGGAATCTGGCGGCGGACTGGTGCAGCCTGGCGGCTCTCTGC

GGCTGTCTTGTGCCGTGTCCGGCAACATCTACAACCGGAACTTCATGGGCTGGTTC

CGGCAGGCCCCCGGAAAAGGCCGCGAAGGCGTGTCCGCCATCTACACGGGCACC

TCCAGAACATATTACGCCGACAGCGTGAAAGGTAGATTCACCATCTCCAGAGACA

ACGCCAAGAACACCGTGTACCTGCAGATGAACTCCCTGAGACCAGAGGACACAG

CTGTGTACTATTGCGCTGCTGATCTGAGGGATGGCTTCTGGGACACCGGCGTGTGG

AACACCTGGGGCCAGGGCACACTGGTCACTGTGTCTTCCGAACCTAAGTCTAGCG

ACAAAACTCATACCAGCCCCCCTAGTCCAGAGATCGTGCTGACCCAGTCTCCAGC

CACACTGTCTCTGTCCCCAGGAGAGAGGGCCACCCTGAGCTGCCGGGCTTCTGAG

AACGTGGGCACATACATCTCCTGGTATCAGCAGAAGCCAGGACAGGCTCCTAGGC

TGCTGATCTACGGCGCTAGCAATAGATATACCGGCATCCCTGCTCGCTTCAGCGGAT

CTGGATCCGGCACAGACTTTACCCTGACAATCTCCAGCCTGGAGCCAGAGGATTT

CGCCGTGTACTATTGTGGCGAGTCCTACGGCCACCTGTATACCTTTGGCGGCGGCA

CAAAGGTGGAGATCAAGCGAACGGTGGCTGCACCATCTGTCTTCATCTTCCCGCC

ATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGG

TAACTCCCAGGAGAGTGTCACAGAGCAGGACAGCAAGGACAGCACCTACAGCCT

CAGCAGCACCCTGACGCTGAGCAAAGCAGACTACGAGAAACACAAAGTCTACGC

CTGCGAAGTCACCCATCAGGGCCTGAGCTCGCCCGTCACAAAGAGCTTCAACAG

GGGAGAGTGT
```

Amino acid sequence of polypeptide chain L3
(SEQ ID NO: 20)

```
EVQLVESGGGLVQPGGSLRLSCAVSGNIYNRNFMGWFRQAPGKGREGVSAIYTGTSR

TYYADSVKGRFTISRDNAKNTVYLQMNSLRPEDTAVYYCAADLRDGFWDTGVWNT

WGQGTLVTVSSEPKSSDKTHTSPPSPEIVLTQSPATLSLSPGERATLSCRASENVGTYIS

WYQQKPGQAPRLLIYGASNRYTGIPARFSGSGSGTDFTLTISSLEPEDFAVYYCGESYG
```

```
HLYTFGGGTKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKS

FNRGEC

DNA sequence of polypeptide chain L4
                                             (SEQ ID NO: 21)
GAGGTGCAGCTGGTCGAGTCTGGCGGTGGCCTGGTTCAGCCCGGCGGCTCCCTGC

GGCTGAGCTGCGCCGTGTCCGGCAACATCTACAACAGAAACTTCATGGGCTGGTT

TAGACAGGCTCCTGGCAAGGGACTGGAAGGCGTGTCCGCCATCTACACCGGCACC

TCTCGGACTTACTACGCCGACTCTGTCAAGGGCAGATTCACCATCTCCCGGGACA

ACTCCAAGAACACAGTGTATCTGCAGATGAACAGCCTGAGAGCCGAGGATACCGC

TGTGTACTACTGCGCTGCTGATCTGAGAGAGGGCTTCTGGGACACCGGCGTGTGG

AATACCTGGGGCCAGGGCACCCTGGTGACCGTGTCTTCTGAACCTAAGTCTAGCG

ACAAAACTCATACCAGCCCCCCTAGTCCAGAGATCGTGCTGACCCAGTCTCCAGC

CACACTGTCTCTGTCCCCAGGAGAGAGGGCCACCCTGAGCTGCCGGGCTTCTGAG

AACGTGGGCACATACATCTCCTGGTATCAGCAGAAGCCAGGACAGGCTCCTAGGC

TGCTGATCTACGGCGCTAGCAATAGATATACCGGCATCCCTGCTCGCTTCAGCGGAT

CTGGATCCGGCACAGACTTTACCCTGACAATCTCCAGCCTGGAGCCAGAGGATTT

CGCCGTGTACTATTGTGGCGAGTCCTACGGCCACCTGTATACCTTTGGCGGCGGCA

CAAAGGTGGAGATCAAGCGAACGGTGGCTGCACCATCTGTCTTCATCTTCCCGCC

ATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGG

TAACTCCCAGGAGAGTGTCACAGAGCAGGACAGCAAGGACAGCACCTACAGCCT

CAGCAGCACCCTGACGCTGAGCAAAGCAGACTACGAGAAACACAAAGTCTACGC

CTGCGAAGTCACCCATCAGGGCCTGAGCTCGCCCGTCACAAAGAGCTTCAACAG

GGGAGAGTGT

Amino acid sequence of polypeptide chain L4
                                             (SEQ ID NO: 22)
EVQLVESGGGLVQPGGSLRLSCAVSGNIYNRNFMGWFRQAPGKGLEGVSAIYTGTSR

TYYADSVKGRFTISRDNSKNTVYLQMNSLRAEDTAVYYCAADLREGFWDTGVWNT

WGQGTLVTVSSEPKSSDKTHTSPPSPEIVLTQSPATLSLSPGERATLSCRASENVGTYIS

WYQQKPGQAPRLLIYGASNRYTGIPARFSGSGSGTDFTLTISSLEPEDFAVYYCGESYG

HLYTFGGGTKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKS

FNRGEC

DNA sequence of polypeptide chain H5
                                             (SEQ ID NO: 23)
GAGGTGCAGCTGGTGCAGTCCGGAGCTGAGGTGAAGAAGCCAGGATCCAGCGTG

AAGGTGAGCTGCAAGGCTAGCGGCTACTCTTTCACCCACCATTGGATCCACTGGG

TGAGGCAGGCTCCTGGACAGGGACTGGAGTGGATGGGCATGATCGACGCTTCCGA

TAGCGAGACAAGACTGTCTCAGAAGTTTAAGGACCGCGTGACCATCACAGCCGAT

AAGTCTACCTCCACAGCTTACATGGAGCTGTCTTCCCTGAGATCCGAGGACACCG

CCGTGTACTATTGTGCTAGGCTGGCCGGTACTATTTCGATTATTGGGGCCAGGGC

ACCACAGTGACAGTGAGCTCTGCCAGCACAAAGGGCCCTTCCGTGTTCCCACTGG
```

-continued
```
CTCCCTGCTCCAGAAGCACATCTGAGTCCACCGCCGCTCTGGGCTGTCTGGTGAA

GGACTACTTCCCTGAGCCAGTGACCGTGTCCTGGAACAGCGGCGCCCTGACATCT

GGCGTGCACACCTTTCCAGCTGTGCTGCAGTCCAGCGGCCTGTACTCCCTGTCTTC

CGTGGTGACAGTGCCCAGCTCTTCCCTGGGCACCAAGACATATACCTGCAACGTG

GACCATAAGCCTTCCAATACCAAGGTGGATAAGAGGGTGGAGAGCAAGTACGGAC

CACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAGGGTGGAGGCGGTAGTGGAGGCGGTGGTTCAGGCGGAGGCGGAT

CTGAAGTGCAGCTGGTGGAATCTGGCGGCGGACTGGTGCAGCCTGGCGGCTCTCT

GCGGCTGTCTTGTGCCGTGTCCGGCAACATCTACAACCGGAACTTCATGGGCTGG

TTCCGGCAGGCCCCCGGAAAAGGCCGCGAAGGCGTGTCCGCCATCTACACGGGC

ACCTCCAGAACATATTACGCCGACAGCGTGAAAGGTAGATTCACCATCTCCAGAG

ACAACGCCAAGAACACCGTGTACCTGCAGATGAACTCCCTGAGACCAGAGGACA

CAGCTGTGTACTATTGCGCTGCTGATCTGAGGGATGGCTTCTGGGACACCGGCGTG

TGGAACACCTGGGGCCAGGGCACACTGGTCACTGTGTCTTCC
```
Amino acid sequence of polypeptide chain H5
(SEQ ID NO: 24)
```
EVQLVQSGAEVKKPGSSVKVSCKASGYSFTHHWIHWVRQAPGQGLEWMGMIDASD

SETRLSQKFKDRVTITADKSTSTAYMELSSLRSEDTAVYYCARLGRYYFDYWGQTT

VTVSSASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPPCPA

PEFEGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKGGGGSGGGGSG

GGGSEVQLVESGGGLVQPGGSLRLSCAVSGNIYNRNFMGWFRQAPGKGREGVSAIY

TGTSRTYYADSVKGRFTISRDNAKNTVYLQMNSLRPEDTAVYYCAADLRDGFWDTG

VWNTWGQGTLVTVSS
```
DNA sequence of polypeptide chain H6
(SEQ ID NO: 25)
```
GAAGTGCAGCTGGTGGAATCTGGCGGCGGACTGGTGCAGCCTGGCGGCTCTCTGC

GGCTGTCTTGTGCCGTGTCCGGCAACATCTACAACCGGAACTTCATGGGCTGGTTC

CGGCAGGCCCCCGGAAAAGGCCGCGAAGGCGTGTCCGCCATCTACACGGGCACC
```

-continued

```
TCCAGAACATATTACGCCGACAGCGTGAAAGGTAGATTCACCATCTCCAGAGACA

ACGCCAAGAACACCGTGTACCTGCAGATGAACTCCCTGAGACCAGAGGACACAG

CTGTGTACTATTGCGCTGCTGATCTGAGGGATGGCTTCTGGGACACCGGCGTGTGG

AACACCTGGGGCCAGGGCACACTGGTCACTGTGTCTTCCGAGAGCAAGTACGGA

CCACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAG
```

Amino acid sequence of polypeptide chain H6
(SEQ ID NO: 26)
```
EVQLVESGGGLVQPGGSLRLSCAVSGNIYNRNFMGWFRQAPGKGREGVSAIYTGTSR

TYYADSVKGRFTISRDNAKNTVYLQMNSLRPEDTAVYYCAADLRDGFWDTGVWNT

WGQGTLVTVSSESKYGPPCPPCPAPEFEGGPSVFLFPPKPKDTLMISRTPEVTCVVVD

VSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMHEALHNH

YTQKSLSLSLGK
```

DNA sequence of polypeptide chain H7
(SEQ ID NO: 27)
```
GAGGTGCAGCTGGTCGAGTCTGGCGGTGGCCTGGTTCAGCCCGGCGGCTCCCTGC

GGCTGAGCTGCGCCGTGTCCGGCAACATCTACAACAGAAACTTCATGGGCTGGTT

TAGACAGGCTCCTGGCAAGGGACTGGAAGGCGTGTCCGCCATCTACACCGGCACC

TCTCGGACTTACTACGCCGACTCTGTCAAGGGCAGATTCACCATCTCCCGGGACA

ACTCCAAGAACACAGTGTATCTGCAGATGAACAGCCTGAGAGCCGAGGATACCGC

TGTGTACTACTGCGCTGCTGATCTGAGAGAGGGCTTCTGGGACACCGGCGTGTGG

AATACCTGGGGCCAGGGCACCCTGGTGACCGTGTCTTCTGAGAGCAAGTACGGAC

CACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG
```

```
-continued
CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAG
```

Amino acid sequence of polypeptide chain H7
(SEQ ID NO: 28)
```
EVQLVESGGGLVQPGGSLRLSCAVSGNIYNRNFMGWFRQAPGKGLEGVSAIYTGTSR

TYYADSVKGRFTISRDNSKNTVYLQMNSLRAEDTAVYYCAADLREGFWDTGVWNT

WGQGTLVTVSSESKYGPPCPPCPAPEFEGGPSVFLFPPKPKDTLMISRTPEVTCVVVD

VSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMHEALHNH

YTQKSLSLSLGK
```

TABLE 4

Linker sequences and IgG4-Fc sequences

| | Sequence | SEQ ID NO: |
|---|---|---|
| DNA sequence of E-Linker | GAACCTAAGTCTAGCGACAAAACTCATACCAGCCCCC CTAGTCCA | 45 |
| Amino acid sequence of E-Linker | EPKSSDKTHTSPPSP | 46 |
| DNA sequence of G15-Linker | GGTGGAGGCGGTAGTGGAGGCGGTGGTTCAGGCGGA GGCGGATCT | 47 |
| Amino acid sequence of G15-Linker | GGGGSGGGGSGGGGS | 48 |
| DNA sequence of IgG4 Fc | GAGAGCAAGTACGGACCACCTTGCCCACCATGTCCAG CTCCTGAGTTTGAGGGAGGACCATCCGTGTTCCTGTTT CCTCCAAAGCCTAAGGACACCCTGATGATCAGCCGGA CACCTGAGGTGACCTGCGTGGTGGTGGACGTGTCTCA GGAGGATCCAGAGGTGCAGTTCAACTGGTACGTGGAT GGCGTGGAGGTGCACAATGCTAAGACCAAGCCAAGA GAGGAGCAGTTTAATTCCACATACCGCGTGGTGAGCG TGCTGACCGTGCTGCATCAGGATTGGCTGAACGGCAA GGAGTATAAGTGCAAGGTGTCCAATAAGGGCCTGCCC AGCTCTATCGAGAAGACAATCAGCAAGGCTAAGGGAC AGCCTAGGGAGCCACAGGTGTACACCCTGCCCCCTTC TCAGGAGGAGATGACAAAGAACCAGGTGTCCCTGAC CTGTCTGGTGAAGGGCTTCTATCCAAGCGACATCGCTG TGGAGTGGGAGTCTAATGGCCAGCCCGAGAACAATTA CAAGACCACACCACCCGTGCTGGACTCTGATGGCTCC TTCTTTCTGTATTCTAGGCTGACAGTGGATAAGTCCCG GTGGCAGGAGGGCAACGTGTTTAGCTGCTCTGTGATG CACGAGGCCCTGCACAATCATTATACCCAGAAGTCCCT GAGCCTGTCTCTGGGCAAG | 49 |
| Amino acid sequence of IgG4 Fc | ESKYGPPCPPCPAPEFEGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIEK TISKAKGQPREPQVYTLPPSQEEMTKNQVSLTCLVKGFY PSDIAVEWESNGQPENNYKTTPPVLDSDGSFFLYSRLTV DKSRWQEGNVFSCSVMHEALHNHYTQKSLSLSLGK | 50 |

Example 2 FACS Affinity Analysis

For the constructed series of bispecific antibodies, the affinity of these samples with antigens was measured by using a flow cytometer. A sample with an initial concentration of 300 nM undergone serial dilution by 3-fold, and then the affinities between samples with different concentrations and PD-1 antigens or CD47 antigens expressed on CHO-K1 cells were separately tested. Then, an antibody-antigen binding curve was generated based on the geometric mean, raw data of four parameters was plotted by using the GRAPHPAD Prism V6.02 software, and a best fitted value program was compiled to analyze $EC_{50}$.

For the affinity analysis of the PD-1 antigen, after the bispecific antibody produced when the PD-1 sdAb was fused to the N-terminus or C-terminus of the heavy chain or light chain of the anti-CD47 mAb was incubated on the CHO-K1 cells expressing the PD-1 antigen, it was found through FACS detection that, compared with a control of the PD-1 sdAb fused to IgG4 Fc (sdAb-PD1a-IgG4PE and sdAb-PD1b-IgG4PE), the affinity between the PD-1 antigen and the bispecific antibody that was produced when the PD1a or PD1b sdAb was fused to the N-terminus of the heavy chain or light chain of the anti-CD47 mAb was significantly higher than that of the sdAb control. The affinity between the PD-1 antigen and the bispecific antibody that was produced when the PD1a or PD1b sdAb was fused to the C-terminus of the heavy chain or light chain of the anti-CD47 mAb was lower than or equivalent to that of the sdAb control (shown in FIG. 1). Therefore, linking the PD-1 sdAb to the N-terminus of the anti-CD47 mAb will enhance the binding of the PD-1 sdAb to the PD-1 antigen, and linking the PD-1 sdAb to the C-terminus of the anti-CD47 mAb will reduce the affinity between the PD-1 sdAb and the PD-1 antigen.

Figure 2:
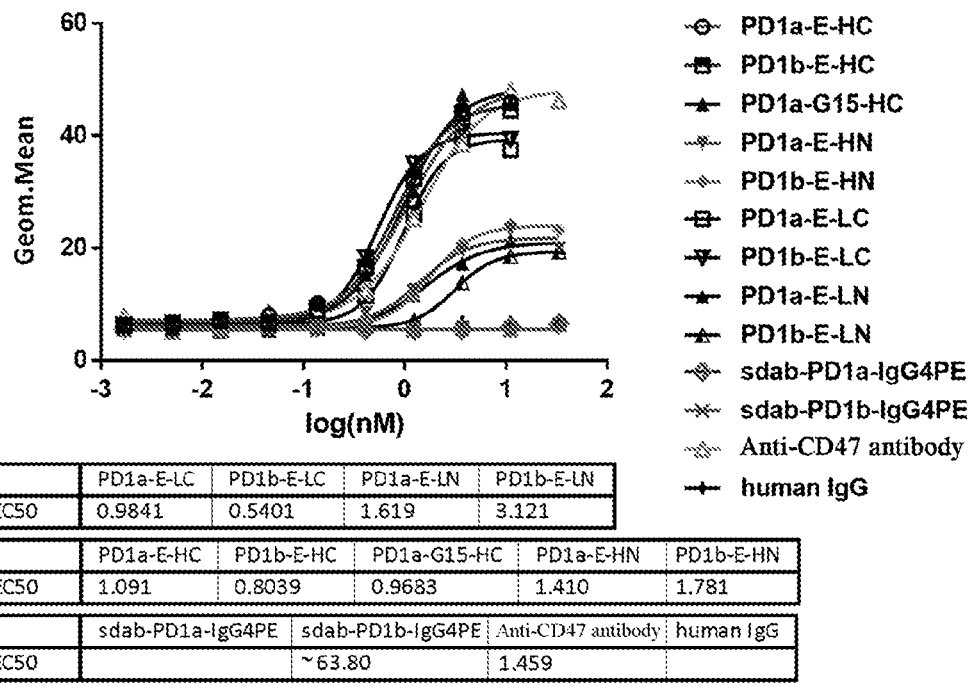
FIG. 2 shows the affinity between a sample and CHO-K1 cells expressing CD47 measured by a flow cytometer.

For the affinity analysis of the CD47 antigen, after the bispecific antibody produced when the PD-1 sdAb was fused to the terminus of the heavy chain or light chain of the anti-CD47 mAb was incubated on the CHO-K1 cells expressing the CD47 antigen, it was found through FACS detection that, compared with a control of the CD47 mAb, the affinity between the CD47 antigen and the bispecific antibody that was produced when the PD1a or PD1b sdAb was fused to the C-terminus of the heavy chain or light chain of the CD47 mAb is significantly higher than that of the control of the CD47 mAb. The affinity between the CD47 antigen and the bispecific antibody that was produced when the PD1a or PD1b sdAb was fused to the N-terminus of the heavy chain or light chain of the CD47 mAb was lower than that of the control of the CD47 mAb (shown in FIG. 2). Therefore, linking the PD-1 sdAb to the C-terminus of the CD47 mAb enhances the binding of the CD47 antibody to the CD47 antigen, and linking the PD-1 sdAb to the N-terminus of the CD47 mAb reduces the affinity between the CD47 antibody and the CD47 antigen.

Example 3 Biological Activity Measurement In Vitro

For the biological activity measurement in vitro of the anti-CD47/anti-PD-1 bispecific antibody, there is no analytical system that can detect both CD47 and PD-1 blockers at the same time. Therefore, the bioassay of the PD-1 blocker is carried out by using the Promega test kit, and then the activity of the bispecific antibody is tested through an anti-CD47 cell phagocytosis experiment.

The Promega PD-1/PD-L1 blocking function reporter gene kit (PD-1/PD-L1 Blockade Bioassay, Promega kit product number J1250) is used in the experiment for testing the in vitro function of the anti-CD47/anti-PD-1 bispecific antibody. The kit detection system consists of two genetically engineered cell lines. The stimulating cell line is PD-L1 aAPC/CHO-K1 cells, which stably express human PD-L1 and a cell surface protein that can activate the homologous TCR in an antigen-independent manner. The effector cell line is the Jurkat T cell line, which stably expresses human PD-1 and an NFAT-induced luciferase reporter gene. When the two types of cells are co-cultured, the interaction of PD-1/PD-L1 inhibits the TCR signal transduction and NFAT-mediated luciferase activity. The addition of the anti-PD-1/PD-L1 antibody can block the binding of PD-1 to PD-L1, thereby enabling the activation of the TCR signaling pathway and the enhancement of the NFAT-mediated luciferase activity, and generating chemiluminescence.

The effector cell line Jurkat T cells were first plated in a 96-well plate, and the anti-CD47/anti-PD-1 bispecific antibody and the stimulating cell line PD-L1 aAPC/CHO-K1 cells were then added. The resulting system was incubated at 37° C. for 6 h. Next, the Bio-Glo™ fluorescence detection reagent was added to the system, and then incubated for 5-10 min at room temperature. Finally, fluorescence signals in the 96-well plate were read by using a chemical fluorescence signal plate reader. The experiment used the form of eight concentrations and triplicated wells, used the relative fluorescence value as the y-axis, and used the concentration of antibody samples as the x-axis, to plot a four-parameter curve. The curve was analyzed by using the GraphPad Prism software to obtain the $EC_{50}$ value of the anti-CD47/anti-PD-1 bispecific antibody sample.

For the cell phagocytosis experiment of the anti-CD47 antibody, PBMCs were first extracted from human peripheral blood by the concentration gradient method. Monocytes were then isolated from the PBMCs by using the whole monocyte isolation kit (Miltenyi Biotech). These monocytes were stimulated into macrophages with GM-CSF within 14 days. On day 14, HL60 cells were stained with the PKH26 dye and then seeded in a 96-well culture plate, MDM was digested from a Petri dish by using Accutase and then added into the culture plate in which HL60 cells stained with PKH26 were seeded, then the anti-CD47/anti-PD-1 bispecific antibody sample after serial dilution was added, and incubated at 37° C. for 1 h to carry out the cell phagocytosis reaction. One hour later, MDM was digested from the cell culture plate and stained with the fluorescently labeled anti-CD11b antibody. The cells in the cell culture plate were then analyzed by using the BD FACSCalibur flow cytometer. The phagocytic percentage was calculated by dividing the number of PKH26 and CD11b double-positive cells by the number of PKH26 single-positive cells. A dose—response curve used the phagocytic percentage as the y-axis and used the concentration of the anti-CD47/anti-PD-1 bispecific antibody as the x-axis, and the GraphPad Prism software was used for analysis to obtain the $EC_{50}$ value and other curve parameters.

Figure 3:
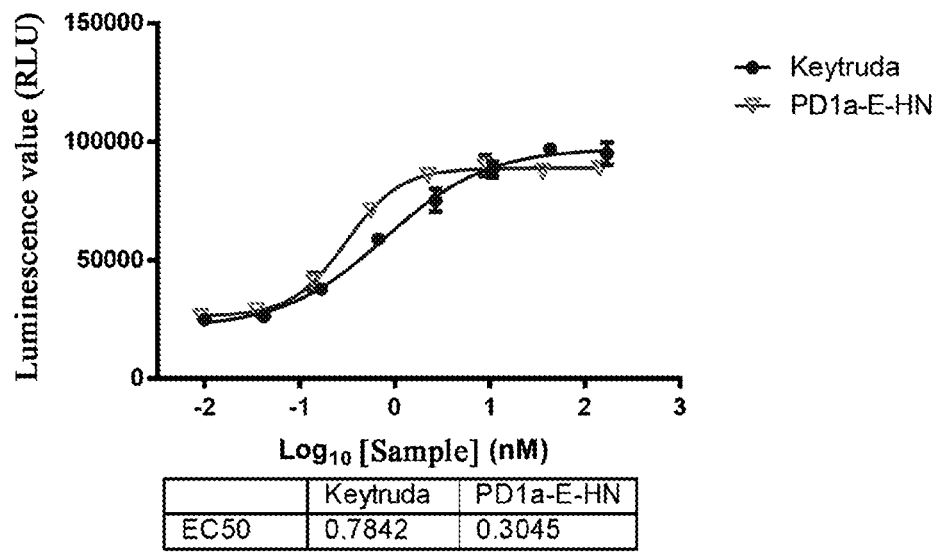
FIG. 3 shows the PD-1 blocking activity of a sample measured by a PD-1/PD-L1 blocking bioassay system.
Figure 4:
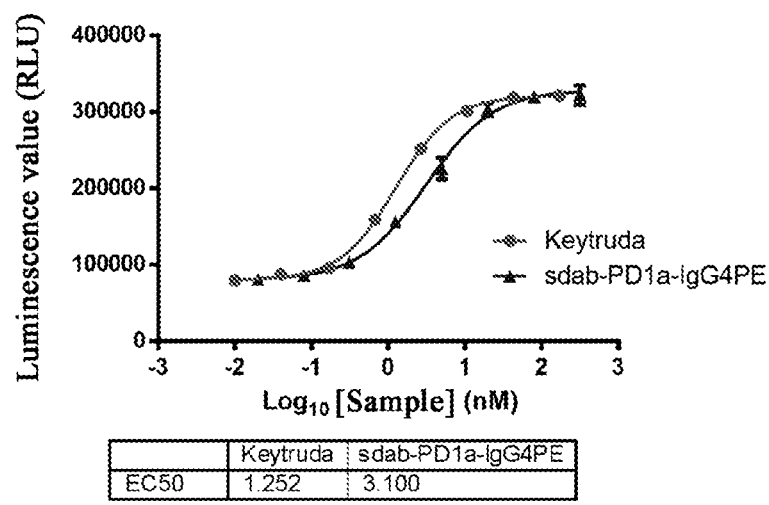
FIG. 4 shows the PD-1 blocking activity of a sample measured by a PD-1/PD-L1 blocking bioassay system.

It was indicated based on the biological activity measurement result of the PD-1/PD-L1 blocker that the biological activity of the bispecific antibody PD1a-E-HN was higher than that of the PD-1 mAb control (Keytruda) (shown in FIG. 3). The sdAb PD1a constructing the bispecific antibody was also fused to IGg4-Fc to produce a fusion protein sdAb-PD1a-IgG4PE to be used as the PD-1 sdAb control. It showed in FIG. 4 that the biological activity of sdAb-PD1a-IgG4PE was lower than that of the PD-1 mAb control (Keytruda), but the biological activity of the bispecific antibody PD1a-E-HN was higher than that of the PD-1 mAb control (Keytruda), indicating that the PD-1 sdAb in the bispecific antibody PD1a-E-HN was fused to the N-terminus of the heavy chain of the anti-CD47 mAb, which could enhance the biological activity of the PD-1 sdAb. It was also indicated based on the FACS affinity analysis result that the affinity of the bispecific antibody with the PD-1 antigen was significantly higher than that of the PD-1 sdAb control. The consistency of affinity and biological activity in vitro further confirms that the bispecific antibody enhances the activity of the PD-1 sdAb.

Figure 5:
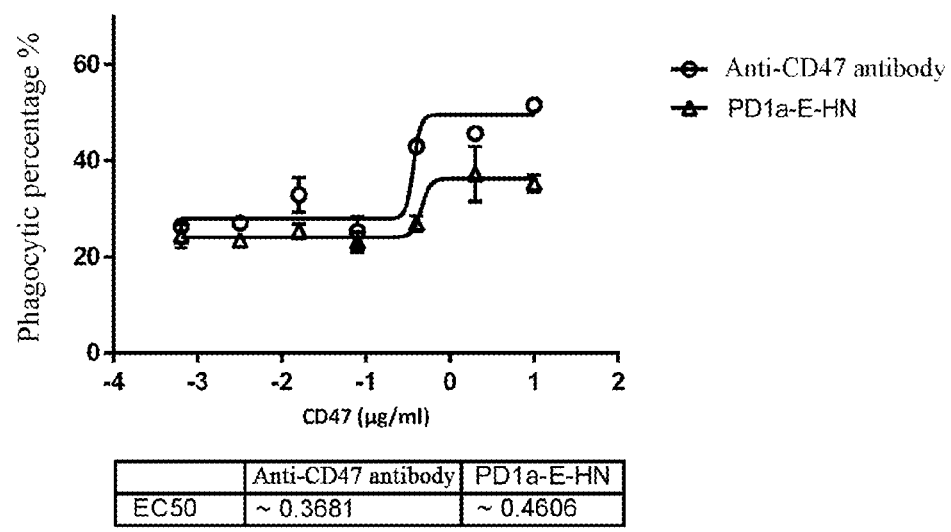
FIG. 5 shows the activity of the bispecific antibody PD1a-E-HN tested by a cell phagocytosis experiment of the anti-CD47 antibody.

It was indicated based on the cell phagocytosis experiment result of the anti-CD47 antibody that the $EC_{50}$ value of the bispecific antibody PD1a-E-HN was slightly lower than that of the CD47 antibody control (shown in FIG. 5). It was indicated based on the FACS affinity analysis result that its affinity was lower than that of the anti-CD47 mAb control, indicating that the decrease in affinity had a certain impact on the anti-CD47 antibody activity of the bispecific antibody, but reduced the red blood cell toxicity of the anti-CD47 antibody to a certain extent.

What is claimed is:

1. An isolated anti-CD47/anti-PD-1 bispecific antigen-binding protein or a fragment thereof, comprising (a) a first antigen binding portion comprising a heavy chain variable region ($V_H$) and a light chain variable region ($V_L$), wherein the $V_H$ and $V_L$ form an antigen binding site that specifically binds to CD47; and (b) a second antigen binding portion comprising a single-domain antibody (sdAb) that specifically binds to PD-1, wherein the first antigen binding portion and the second antigen binding portion are fused to each other; wherein
the $V_H$ of the first antigen binding portion comprises heavy chain complementarity-determining regions HCDR1, HCDR2, and HCDR3, the amino acid sequences of the HCDR1, HCDR2, and HCDR3 are respectively as set forth in SEQ ID NO:33, SEQ ID NO:34, and SEQ ID NO: 35; and the $V_L$ of the first antigen binding portion comprises light chain complementarity-determining regions LCDR1, LCDR2, and LCDR3, the amino acid sequences of the LCDR1, LCDR2, and LCDR3 are respectively as set forth in SEQ ID NO:36, SEQ ID NO: 37, and SEQ ID NO:38; and/or
the sdAb of the second antigen binding portion comprises complementarity-determining regions CDR1, CDR2, and CDR3, the amino acid sequences of CDR1, CDR2 and CDR3 are respectively as set forth in SEQ ID NO:39, SEQ ID NO: 40 and SEQ ID NO: 41, or the amino acid sequences of CDR1, CDR2 and CDR3 are respectively as set forth in SEQ ID NO: 42, SEQ ID NO: 43 and SEQ ID NO: 44.

2. The isolated bispecific antigen-binding protein or the fragment thereof according to claim 1, wherein the first antigen binding portion is a full-length antibody comprising two heavy chains and two light chains, the heavy chain comprises $V_H$, and the light chain comprises $V_L$.

3. The isolated bispecific antigen-binding protein or the fragment thereof according to claim 2, wherein:
the C-terminus of the second antigen binding portion is fused to the N-terminus of at least one heavy chain of the first antigen binding portion or the N-terminus of at least one light chain of the first antigen binding portion; or
the N-terminus of the second antigen binding portion is fused to the C-terminus of at least one heavy chain of the first antigen binding portion or the C-terminus of at least one light chain of the first antigen binding portion.

4. The isolated bispecific antigen-binding protein or the fragment thereof according to claim 1, wherein the first antigen binding portion and the second antigen binding portion are fused by a peptide bond or a peptide linker.

5. The isolated bispecific antigen-binding protein or the fragment thereof according to claim 4, wherein the peptide linker is selected from a mutated human IgG1 hinge region or a GS linker.

6. The isolated bispecific antigen-binding protein or the fragment thereof according to claim 1, wherein the $V_H$ of the first antigen binding portion comprises heavy chain complementarity-determining regions HCDR1, HCDR2, and HCDR3, the amino acid sequences of the HCDR1, HCDR2, and HCDR3 are respectively as set forth in SEQ ID NO: 33, SEQ ID NO:34, and SEQ ID NO:35; and the $V_L$ of the first antigen binding portion comprises light chain complementarity-determining regions LCDR1, LCDR2, and LCDR3, the amino acid sequences of the LCDR1, LCDR2, and LCDR3 are respectively as set forth in SEQ ID NO: 36, SEQ ID NO:37, and SEQ ID NO:38, and wherein the heavy chain of the first antigen binding portion comprises a sequence that is at least 95% identical to the amino acid sequence as set forth in SEQ ID NO:4, and the light chain of the first antigen binding portion comprises a sequence that is at least 95% identical to the amino acid sequence as set forth in SEQ ID NO:6.

7. The isolated bispecific antigen-binding protein or the fragment thereof according to claim 1, the sdAb of the second antigen binding portion comprises complementarity-determining regions CDR1, CDR2, and CDR3, the amino acid sequences of CDR1, CDR2 and CDR3 are respectively as set forth in SEQ ID NO:39, SEQ ID NO: 40 and SEQ ID NO: 41, or the amino acid sequences of CDR1, CDR2 and CDR3 are respectively as set forth in SEQ ID NO: 42, SEQ ID NO: 43 and SEQ ID NO: 44, and wherein the second antigen binding portion comprises a sequence that is at least 95% identical to the amino acid sequence as set forth in SEQ ID NO:30 or SEQ ID NO:32.

8. The isolated bispecific antigen-binding protein or the fragment thereof according to claim 1, wherein the first antigen binding portion comprises a human, humanized, or chimeric antibody or a fragment thereof, and the sdAb of the second antigen binding portion is camelid, chimeric, humanized, or human antibody.

9. The isolated bispecific antigen-binding protein or the fragment thereof according to claim 1, comprising an anti-CD47 antibody and an anti-PD-1 sdAb, wherein the $V_H$ of the first antigen binding portion comprises heavy chain complementarity-determining regions HCDR1, HCDR2, and HCDR3, the amino acid sequences of the HCDR1, HCDR2, and HCDR3 are respectively as set forth in SEQ ID NO:33, SEQ ID NO: 34, and SEQ ID NO:35; and the $V_L$ of the first antigen binding portion comprises light chain complementarity-determining regions LCDR1, LCDR2, and LCDR3, the amino acid sequences of the LCDR1, LCDR2, and LCDR3 are respectively as set forth in SEQ ID NO:36, SEQ ID NO: 37, and SEQ ID NO:38; and the sdAb of the second antigen binding portion comprises complementarity-determining regions CDR1, CDR2, and CDR3, the amino acid sequences of CDR1, CDR2 and CDR3 are respectively as set forth in SEQ ID NO:39, SEQ ID NO: 40 and SEQ ID NO: 41, or the amino acid sequences of CDR1, CDR2 and CDR3 are respectively as set forth in SEQ ID NO: 42, SEQ ID NO: 43 and SEQ ID NO: 44; and wherein the N-terminus of the anti-PD-1 sdAb fused to the C-terminus of two heavy chains of the anti-CD47 antibody, wherein the heavy chain fusion polypeptide comprises a sequence that is at least 95% identical to the amino acid sequence as set forth in SEQ ID NO:8, SEQ ID NO:10, or SEQ ID NO:24, and the light chain polypeptide comprises a sequence that is at least 95% identical to the amino acid sequence as set forth in SEQ ID NO:6;

the C-terminus of the anti-PD-1 sdAb fused to the N-terminus of two heavy chains of the anti-CD47 antibody, wherein the heavy chain fusion polypeptide comprises a sequence that is at least 95% identical to the amino acid sequence as set forth in SEQ ID NO:12 or SEQ ID NO:14, and the light chain polypeptide comprises a sequence that is at least 95% identical to the amino acid sequence as set forth in SEQ ID NO:6;

the N-terminus of the anti-PD-1 sdAb fused to the C-terminus of two light chains of the anti-CD47 antibody, wherein the light chain fusion polypeptide comprises a sequence that is at least 95% identical to the amino acid sequence as set forth in SEQ ID NO: 16 or SEQ ID NO:18, and the heavy chain polypeptide comprises a sequence that is at least 95% identical to the amino acid sequence as set forth in SEQ ID NO:4; or the C-terminus of the anti-PD-1 sdAb fused to the N-terminus of two light chains of the anti-CD47 antibody, wherein the light chain fusion polypeptide comprises a sequence that is at least 95% identical to the amino acid sequence as set forth in SEQ ID NO:20 or SEQ ID NO:22, and the heavy chain polypeptide comprises a sequence that is at least 95% identical to the amino acid sequence as set forth in SEQ ID NO:4.

10. An isolated polynucleotide encoding the anti-CD47/anti-PD-1 bispecific antigen-binding protein or the fragment thereof according to claim 1.

11. A vector comprising the isolated polynucleotide according to claim 10.

12. A host cell comprising the isolated polynucleotide according to claim 10.

13. A method for producing an isolated anti-CD47/anti-PD-1 bispecific antigen-binding protein or a fragment thereof, comprising culturing the host cell according to claim 12 under proper conditions, and recovering an antibody or a fragment thereof from the cell or a cell culture medium.

14. A pharmaceutical composition, comprising the bispecific antigen-binding protein or the fragment thereof according to claim 1 and a pharmaceutically acceptable carrier.

15. A method of treating diseases related to abnormal expression of CD47 and/or PD-1, comprising administrating to a subject in need thereof an effective amount of the anti-CD47/anti-PD-1 bispecific antigen-binding protein or the fragment thereof according to claim 1.

16. The method according to claim 15, wherein the diseases related to abnormal expression of CD47 and/or PD-1 are cancers.

17. The method according to claim 16, wherein the cancers are solid tumors.

18. The isolated bispecific antigen binding protein or a fragment thereof according to claim 5, wherein an amino acid sequence of the peptide linker is as set forth in SEQ ID NO:46 or SEQ ID NO:48.

* * * * *

SEQUENCE LISTING

<160> NUMBER OF SEQ ID NOS: 50

<210> SEQ ID NO 1
<211> LENGTH: 57
<212> TYPE: DNA
<213> ORGANISM: Artificial Sequence
<220> FEATURE:
<223> OTHER INFORMATION: DNA sequence of secretion signal peptide

<400> SEQUENCE: 1
atgggctggt cctgcatcat cctgttcctg gtggctaccg ccaccggcgt gcactcc        57

<210> SEQ ID NO 2
<211> LENGTH: 19
<212> TYPE: PRT
<213> ORGANISM: Artificial Sequence
<220> FEATURE:
<223> OTHER INFORMATION: Amino acid sequence of secretion signal peptide

<400> SEQUENCE: 2

Met Gly Trp Ser Cys Ile Ile Leu Phe Leu Val Ala Thr Ala Thr Gly
1               5                   10                  15

Val His Ser

<210> SEQ ID NO 3
<211> LENGTH: 1332
<212> TYPE: DNA
<213> ORGANISM: Artificial Sequence
<220> FEATURE:
<223> OTHER INFORMATION: DNA sequence of polypeptide chain H0

<400> SEQUENCE: 3
gaggtgcagc tggtgcagtc cggagctgag gtgaagaagc caggatccag cgtgaaggtg        60
agctgcaagg ctagcggcta ctctttcacc caccattgga tccactgggt gaggcaggct       120
cctggacagg gactggagtg gatgggcatg atcgacgctt ccgatagcga gacaagactg       180
tctcagaagt ttaaggaccg cgtgaccatc acagccgata gtctacctc cacagcttac        240 atggagctgt cttccctgag atccgaggac accgccgtgt actattgtgc taggctgggc       300
cggtactatt tcgattattg gggccagggc accacagtga cagtgagctc tgccagcaca       360
aagggccctt ccgtgttccc actggctccc tgctccagaa gcacatctga gtccaccgcc       420
gctctgggct gtctggtgaa ggactacttc cctgagccca tgaccgtgtc ctggaacagc       480
ggcgccctga catctggcgt gcacaccttt ccagctgtgc tgcagtccag cggcctgtac       540
tccctgtctt ccgtggtgac agtgcccagc tcttccctgg gcaccaagac atatacctgc       600
aacgtggacc ataagccttc aataccaag gtggataaga gggtggagag caagtacgga        660
ccaccttgcc caccatgtcc agctcctgag tttgagggag accatccgt gttcctgttt        720 cctccaaagc ctaaggacac cctgatgatc agccggacac ctgaggtgac ctgcgtggtg       780

```
gtggacgtgt ctcaggagga tccagaggtg cagttcaact ggtacgtgga tggcgtggag      840
gtgcacaatg ctaagaccaa gccaagagag gagcagttta attccacata ccgcgtggtg      900
agcgtgctga ccgtgctgca tcaggattgg ctgaacggca aggagtataa gtgcaaggtg      960
tccaataagg gcctgcccag ctctatcgag aagacaatca gcaaggctaa gggacagcct     1020
agggagccac aggtgtacac cctgcccccct tctcaggagg agatgacaaa gaaccaggtg     1080
tccctgacct gtctggtgaa gggcttctat ccaagcgaca tcgctgtgga gtgggagtct     1140
aatggccagc ccgagaacaa ttacaagacc acaccaccccg tgctggactc tgatggctcc     1200
ttctttctgt attctaggct gacagtggat aagtcccggt ggcaggaggg caacgtgttt     1260
agctgctctg tgatgcacga ggccctgcac aatcattata cccagaagtc cctgagcctg     1320
tctctgggca ag                                                         1332
```

<210> SEQ ID NO 4
<211> LENGTH: 444
<212> TYPE: PRT
<213> ORGANISM: Artificial Sequence
<220> FEATURE:
<223> OTHER INFORMATION: Amino acid sequence of polypeptide chain H0

<400> SEQUENCE: 4

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
                20                  25                  30

Trp Ile His Trp Val Arg Gln Ala Pro Gly Gln Gly Leu Glu Trp Met
            35                  40                  45

Gly Met Ile Asp Ala Ser Asp Ser Glu Thr Arg Leu Ser Gln Lys Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
```

```
                260                 265                 270
Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 5
<211> LENGTH: 642
<212> TYPE: DNA
<213> ORGANISM: Artificial Sequence
<220> FEATURE:
<223> OTHER INFORMATION: DNA sequence of polypeptide chain L0

<400> SEQUENCE: 5
gagatcgtgc tgacccagtc tccagccaca ctgtctctgt ccccaggaga gagggccacc      60
ctgagctgcc gggcttctga gaacgtgggc acatacatct cctggtatca gcagaagcca     120
ggacaggctc ctaggctgct gatctacggc gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 6
<211> LENGTH: 214
<212> TYPE: PRT
<213> ORGANISM: Artificial Sequence
<220> FEATURE:
<223> OTHER INFORMATION: Amino acid sequence of polypeptide chain L0

<400> SEQUENCE: 6

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Glu Asn Val Gly Thr Tyr
         20                  25                  30

Ile Ser Trp Tyr Gln Gln Lys Pro Gly Gln Ala Pro Arg Leu Leu Ile
     35                  40                  45

Tyr Gly Ala Ser Asn Arg Tyr Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
             85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 1746
<212> TYPE: DNA
<213> ORGANISM: Artificial Sequence
<220> FEATURE:
<223> OTHER INFORMATION: DNA sequence of polypeptide chain H1

<400> SEQUENCE: 7
gaggtgcagc tggtgcagtc cggagctgag gtgaagaagc caggatccag cgtgaaggtg    60
agctgcaagg ctagcggcta ctctttcacc caccattgga tccactgggt gaggcaggct   120
cctggacagg gactggagtg gatgggcatg atcgacgctt ccgatagcga gacaagactg   180
tctcagaagt ttaaggaccg cgtgaccatc acagccgata gtctacctc cacagcttac   240 atggagctgt cttccctgag atccgaggac accgccgtgt actattgtgc taggctgggc   300
cggtactatt tcgattattg gggccagggc accacagtga cagtgagctc tgccagcaca   360
aagggcccct tccgtgttcc cactggctcc ctgctccaga agcacatctga gtccaccgcc   420 gctctgggct gtctggtgaa ggactacttc cctgagccag tgaccgtgtc ctggaacagc   480
ggcgccctga catctggcgt gcacaccttt ccagctgtgc tgcagtccag cggcctgtac   540
tccctgtctt ccgtggtgac agtgcccagc tcttccctgg caccaagac atatacctgc   600 aacgtggacc ataagccttc caataccaag gtggataaga gggtggagag caagtacgga   660
ccaccttgcc caccatgtcc agctcctgag tttgagggag accatccgt gttcctgttt   720 cctccaaagc ctaaggacac cctgatgatc agccggacac tgaggtgac ctgcgtggtg   780 gtggacgtgt ctcaggagga tccagaggtg cagttcaact ggtacgtgga tggcgtggag   840
gtgcacaatg ctaagaccaa gccaagagag gagcagttta attccacata ccgcgtggtg   900

```
agcgtgctga ccgtgctgca tcaggattgg ctgaacggca aggagtataa gtgcaaggtg      960
tccaataagg gcctgcccag ctctatcgag aagacaatca gcaaggctaa gggacagcct     1020
agggagccac aggtgtacac cctgcccect tctcaggagg agatgacaaa gaaccaggtg     1080
tccctgacct gtctggtgaa gggcttctat ccaagcgaca tcgctgtgga gtgggagtct     1140
aatggccagc ccgagaacaa ttacaagacc acaccacccg tgctggactc tgatggctcc     1200
ttctttctgt attctaggct gacagtggat aagtcccggt ggcaggaggg caacgtgttt     1260
agctgctctg tgatgcacga ggccctgcac aatcattata cccagaagtc cctgagcctg     1320
tctctgggca aggaacctaa gtctagcgac aaaactcata ccagcccccc tagtccagaa     1380
gtgcagctgg tggaatctgg cggcggactg gtgcagcctg gcggctctct gcggctgtct     1440
tgtgccgtgt ccggcaacat ctacaaccgg aacttcatgg gctggttccg gcaggccccc     1500
ggaaaaggcc gcgaaggcgt gtccgccatc tacacgggca cctccagaac atattacgcc     1560
gacagcgtga aggtagattc caccatctcc agagacaacg ccaagaacac cgtgtacctg     1620
cagatgaact ccctgagacc agaggacaca gctgtgtact attgcgctgc tgatctgagg     1680
gatggcttct gggacaccgg cgtgtggaac acctggggcc agggcacact ggtcactgtg     1740
tcttcc                                                                 1746

<210> SEQ ID NO 8
<211> LENGTH: 582
<212> TYPE: PRT
<213> ORGANISM: Artificial Sequence
<220> FEATURE:
<223> OTHER INFORMATION: Amino acid sequence of polypeptide chain H1

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205
```

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Glu Pro Lys Ser
        435                 440                 445

Ser Asp Lys Thr His Thr Ser Pro Pro Ser Pro Glu Val Gln Leu Val
    450                 455                 460

Glu Ser Gly Gly Gly Leu Val Gln Pro Gly Gly Ser Leu Arg Leu Ser
465                 470                 475                 480

Cys Ala Val Ser Gly Asn Ile Tyr Asn Arg Asn Phe Met Gly Trp Phe
                485                 490                 495

Arg Gln Ala Pro Gly Lys Gly Arg Glu Gly Val Ser Ala Ile Tyr Thr
            500                 505                 510

Gly Thr Ser Arg Thr Tyr Tyr Ala Asp Ser Val Lys Gly Arg Phe Thr
        515                 520                 525

Ile Ser Arg Asp Asn Ala Lys Asn Thr Val Tyr Leu Gln Met Asn Ser
    530                 535                 540

Leu Arg Pro Glu Asp Thr Ala Val Tyr Tyr Cys Ala Ala Asp Leu Arg
545                 550                 555                 560

Asp Gly Phe Trp Asp Thr Gly Val Trp Asn Thr Trp Gly Gln Gly Thr
                565                 570                 575

Leu Val Thr Val Ser Ser
            580

<210> SEQ ID NO 9
<211> LENGTH: 1746
<212> TYPE: DNA
<213> ORGANISM: Artificial Sequence
<220> FEATURE:

<223> OTHER INFORMATION: DNA sequence of polypeptide chain H2

<400> SEQUENCE: 9

```
gaggtgcagc tggtgcagtc cggagctgag gtgaagaagc caggatccag cgtgaaggtg      60
agctgcaagg ctagcggcta ctctttcacc caccattgga tccactgggt gaggcaggct     120
cctggacagg gactggagtg gatgggcatg atcgacgctt ccgatagcga gacaagactg     180
tctcagaagt ttaaggaccg cgtgaccatc acagccgata agtctacctc cacagcttac     240
atggagctgt cttccctgag atccgaggac accgccgtgt actattgtgc taggctgggc     300
cggtactatt tcgattattg gggccagggc accacagtga cagtgagctc tgccagcaca     360
aagggccctt ccgtgttccc actggctccc tgctccagaa gcacatctga gtccaccgcc     420
gctctgggct gtctggtgaa ggactacttc cctgagccag tgaccgtgtc ctggaacagc     480
ggcgccctga catctggcgt gcacaccttt ccagctgtgc tgcagtccag cggcctgtac     540
tccctgtctt ccgtggtgac agtgcccagc tcttccctgg gcaccaagac atatacctgc     600
aacgtggacc ataagccttc aataccaagg tggataaga gggtggagag caagtacgga      660
ccaccttgcc caccatgtcc agctcctgag tttgagggag gaccatccgt gttcctgttt      720
cctccaaagc ctaaggacac cctgatgatc agccggacac tgaggtgac ctgcgtggtg      780
gtggacgtgt ctcaggagga tccagaggtg cagttcaact ggtacgtgga tggcgtggag     840
gtgcacaatg ctaagaccaa gccaagagag gagcagtttta attccacata ccgcgtggtg    900
agcgtgctga ccgtgctgca tcaggattgg ctgaacggca aggagtataa gtgcaaggtg    960
tccaataagg gcctgcccag ctctatcgag aagacaatca gcaaggctaa gggacagcct   1020
agggagccac aggtgtacac cctgcccct tctcaggagg agatgacaaa gaaccaggtg  1080
tccctgacct gtctggtgaa gggcttctat ccaagcgaca tcgctgtgga gtgggagtct  1140
aatggccagc ccgagaacaa ttacaagacc acaccacccg tgctggactc tgatggctcc  1200
ttctttctgt attctaggct gacagtggat aagtcccgt ggcaggaggg caacgtgttt   1260
agctgctctg tgatgcacga ggccctgcac aatcattata cccagaagtc cctgagcctg   1320
tctctgggca aggaacctaa gtctagcgac aaaactcata ccagcccccc tagtccagag  1380
gtgcagctgg tcgagtctgg cggtggcctg gttcagcccg gcggctccct gcggctgagc  1440
tgcgccgtgt ccggcaacat ctacaacaga aacttcatgg gctggtttag acaggctcct  1500
ggcaagggac tggaaggcgt gtccgccatc tacaccggca cctctcggac ttactacgcc  1560
gactctgtca agggcagatt caccatctcc cgggacaact ccaagaacac agtgtatctg  1620
cagatgaaca gcctgagagc cgaggatacc gctgtgtact actgcgctgc tgatctgaga  1680
gagggcttct gggacaccgg cgtgtggaat acctggggcc agggcaccct ggtgaccgtg  1740
tcttct                                                              1746
```

<210> SEQ ID NO 10
<211> LENGTH: 582
<212> TYPE: PRT
<213> ORGANISM: Artificial Sequence
<220> FEATURE:
<223> OTHER INFORMATION: Amino acid sequence of polypeptide chain H2

<400> SEQUENCE: 10

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30
```

```
Trp Ile His Trp Val Arg Gln Ala Pro Gly Gln Gly Leu Glu Trp Met
        35                  40                  45
Gly Met Ile Asp Ala Ser Asp Ser Glu Thr Arg Leu Ser Gln Lys Phe
    50                  55                  60
Lys Asp Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Leu Gly Arg Tyr Tyr Phe Asp Tyr Trp Gly Gln Gly Thr Thr
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys Glu Pro Lys Ser
        435                 440                 445
```

Ser Asp Lys Thr His Thr Ser Pro Ser Pro Glu Val Gln Leu Val
450                 455                 460

Glu Ser Gly Gly Gly Leu Val Gln Pro Gly Gly Ser Leu Arg Leu Ser
465                 470                 475                 480

Cys Ala Val Ser Gly Asn Ile Tyr Asn Arg Asn Phe Met Gly Trp Phe
                485                 490                 495

Arg Gln Ala Pro Gly Lys Gly Leu Glu Gly Val Ser Ala Ile Tyr Thr
            500                 505                 510

Gly Thr Ser Arg Thr Tyr Tyr Ala Asp Ser Val Lys Gly Arg Phe Thr
        515                 520                 525

Ile Ser Arg Asp Asn Ser Lys Asn Thr Val Tyr Leu Gln Met Asn Ser
530                 535                 540

Leu Arg Ala Glu Asp Thr Ala Val Tyr Tyr Cys Ala Ala Asp Leu Arg
545                 550                 555                 560

Glu Gly Phe Trp Asp Thr Gly Val Trp Asn Thr Trp Gly Gln Gly Thr
                565                 570                 575

Leu Val Thr Val Ser Ser
            580

<210> SEQ ID NO 11
<211> LENGTH: 1746
<212> TYPE: DNA
<213> ORGANISM: Artificial Sequence
<220> FEATURE:
<223> OTHER INFORMATION: DNA sequence of polypeptide chain H3

<400> SEQUENCE: 11
gaagtgcagc tggtggaatc tggcggcgga ctggtgcagc tggcggctc tgcggctg         60 tcttgtgccg tgtccggcaa catctacaac cggaacttca tgggctggtt ccggcaggcc    120
cccggaaaag gccgcgaagg cgtgtccgcc atctacacgg gcacctccag aacatattac    180
gccgacagcg tgaaaggtag attcaccatc tccagagaca cgccaagaa caccgtgtac    240 ctgcagatga actccctgag accagaggac acagctgtgt actattgcgc tgctgatctg    300
agggatggct tctgggacac cggcgtgtgg aacacctggg gccagggcac actggtcact    360
gtgtcttccg aacctaagtc tagcgacaaa actcatacca gcccccctag tccagaggtg    420
cagctggtgc agtccggagc tgaggtgaag aagccaggat ccagcgtgaa ggtgagctgc    480
aaggctagcg gctactcttt cacccaccat tggatccact gggtgaggca ggctcctgga    540
cagggactgg agtggatggg catgatcgac gcttccgata gcgagacaag actgtctcag    600
aagtttaagg accgcgtgac catcacagcc gataagtcta cctccacagc ttacatggag    660
ctgtcttccc tgagatccga ggacaccgcc gtgtactatt gtgctaggct gggccggtac    720
tatttcgatt attggggcca gggcaccaca gtgacagtga gctctgccag cacaaagggc    780
ccttccgtgt tcccactggc tcctgctcc agaagcacat ctgagtccac cgccgctctg    840
ggctgtctgg tgaaggacta cttccctgag ccagtgaccg tgtcctggaa cagcggcgcc    900
ctgacatctg gcgtgcacac ctttccagct gtgctgcagt ccagcggcct gtactccctg    960
tcttccgtgg tgacagtgcc cagctcttcc ctgggcacca agacatatac ctgcaacgtg   1020
gaccataagc cttccaatac caaggtggat aagagggtgg agagcaagta cggaccacct   1080
tgcccaccat gtccagctcc tgagtttgag ggaggaccat ccgtgttcct gtttcctcca   1140
aagcctaagg acaccctgat gatcagccgg acacctgagg tgacctgcgt ggtggtggac   1200
gtgtctcagg aggatcccga ggtgcagttc aactggtacg tggatggcgt ggaggtgcac   1260

```
aatgctaaga ccaagccaag agaggagcag tttaattcca cataccgcgt ggtgagcgtg    1320
ctgaccgtgc tgcatcagga ttggctgaac ggcaaggagt ataagtgcaa ggtgtccaat    1380
aagggcctgc ccagctctat cgagaagaca atcagcaagg ctaagggaca gcctagggag    1440
ccacaggtgt acaccctgcc ccttctcag gaggagatga caaagaacca ggtgtccctg    1500
acctgtctgg tgaagggctt ctatccaagc gacatcgctg tggagtggga gtctaatggc    1560
cagcccgaga caattacaa gaccacacca cccgtgctgg actctgatgg ctccttcttt    1620
ctgtattcta ggctgacagt ggataagtcc cggtggcagg agggcaacgt gtttagctgc    1680
tctgtgatgc acgaggccct gcacaatcat tatacccaga agtccctgag cctgtctctg    1740
ggcaag                                                              1746
```

<210> SEQ ID NO 12
<211> LENGTH: 582
<212> TYPE: PRT
<213> ORGANISM: Artificial Sequence
<220> FEATURE:
<223> OTHER INFORMATION: Amino acid sequence of polypeptide chain H3

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Arg Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Pro Lys Ser Ser
        115                 120                 125

Asp Lys Thr His Thr Ser Pro Pro Ser Pro Glu Val Gln Leu Val Gln
    130                 135                 140

Ser Gly Ala Glu Val Lys Lys Pro Gly Ser Ser Val Lys Val Ser Cys
145                 150                 155                 160

Lys Ala Ser Gly Tyr Ser Phe Thr His His Trp Ile His Trp Val Arg
                165                 170                 175

Gln Ala Pro Gly Gln Gly Leu Glu Trp Met Gly Met Ile Asp Ala Ser
            180                 185                 190

Asp Ser Glu Thr Arg Leu Ser Gln Lys Phe Lys Asp Arg Val Thr Ile
        195                 200                 205

Thr Ala Asp Lys Ser Thr Ser Thr Ala Tyr Met Glu Leu Ser Ser Leu
    210                 215                 220

Arg Ser Glu Asp Thr Ala Val Tyr Tyr Cys Ala Arg Leu Gly Arg Tyr
225                 230                 235                 240

Tyr Phe Asp Tyr Trp Gly Gln Gly Thr Thr Val Thr Val Ser Ser Ala
                245                 250                 255

Ser Thr Lys Gly Pro Ser Val Phe Pro Leu Ala Pro Cys Ser Arg Ser
            260                 265                 270
```

-continued

```
Thr Ser Glu Ser Thr Ala Ala Leu Gly Cys Leu Val Lys Asp Tyr Phe
            275                 280                 285

Pro Glu Pro Val Thr Val Ser Trp Asn Ser Gly Ala Leu Thr Ser Gly
        290                 295                 300

Val His Thr Phe Pro Ala Val Leu Gln Ser Ser Gly Leu Tyr Ser Leu
305                 310                 315                 320

Ser Ser Val Val Thr Val Pro Ser Ser Ser Leu Gly Thr Lys Thr Tyr
                325                 330                 335

Thr Cys Asn Val Asp His Lys Pro Ser Asn Thr Lys Val Asp Lys Arg
            340                 345                 350

Val Glu Ser Lys Tyr Gly Pro Pro Cys Pro Pro Cys Pro Ala Pro Glu
        355                 360                 365

Phe Glu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser Gln Glu Asp Pro Glu Val Gln Phe Asn Trp Tyr Val Asp Gly
                405                 410                 415

Val Glu Val His Asn Ala Lys Thr Lys Pro Arg Glu Glu Gln Phe Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Gly Leu Pro
    450                 455                 460

Ser Ser Ile Glu Lys Thr Ile Ser Lys Ala Lys Gly Gln Pro Arg Glu
465                 470                 475                 480

Pro Gln Val Tyr Thr Leu Pro Pro Ser Gln Glu Glu Met Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Arg
    530                 535                 540

Leu Thr Val Asp Lys Ser Arg Trp Gln Glu Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Leu Gly Lys
            580
```

<210> SEQ ID NO 13
<211> LENGTH: 1746
<212> TYPE: DNA
<213> ORGANISM: Artificial Sequence
<220> FEATURE:
<223> OTHER INFORMATION: DNA sequence of polypeptide chain H4

<400> SEQUENCE: 13

```
gaggtgcagc tggtcgagtc tggcggtggc ctggttcagc ccggcggctc cctgcggctg      60
agctgcgccg tgtccggcaa catctacaac agaaacttca tgggctggtt tagacaggct     120
cctggcaagg gactggaagg cgtgtccgcc atctacaccg gcacctctcg gacttactac     180
gccgactctg tcaagggcag attcaccatc tcccgggaca actccaagaa cacagtgtat     240
ctgcagatga acagcctgag agccgaggat accgctgtgt actactgcgc tgctgatctg     300
```

```
agagagggct tctgggacac cggcgtgtgg aatacctggg gccagggcac cctggtgacc    360
gtgtcttctg aacctaagtc tagcgacaaa actcatacca gccccctag tccagaggtg    420 cagctggtgc agtccggagc tgaggtgaag aagccaggat ccagcgtgaa ggtgagctgc    480
aaggctagcg gctactcttt cacccaccat tggatccact gggtgaggca ggctcctgga    540
cagggactgg agtggatggg catgatcgac gcttccgata gcgagacaag actgtctcag    600
aagtttaagg accgcgtgac catcacagcc gataagtcta cctccacagc ttacatggag    660
ctgtcttccc tgagatccga ggacaccgcc gtgtactatt gtgctaggct gggccggtac    720
tatttcgatt attggggcca gggcaccaca gtgacagtga gctctgccag cacaaagggc    780
ccttccgtgt tcccactggc tcctgctcc agaagcacat ctgagtccac cgccgctctg    840
ggctgtctgg tgaaggacta cttccctgag ccagtgaccg tgtcctggaa cagcggcgcc    900
ctgacatctg gcgtgcacac ctttccagct gtgctgcagt ccagcggcct gtactccctg    960
tcttccgtgg tgacagtgcc cagctcttcc ctgggcacca agacatatac ctgcaacgtg   1020
gaccataagc cttccaatac caaggtggat aagagggtgg agagcaagta cggaccacct   1080
tgcccaccat gtccagctcc tgagtttgag ggaggaccat ccgtgttcct gtttcctcca   1140
aagcctaagg acaccctgat gatcagccgg acacctgagg tgacctgcgt ggtggtggac   1200
gtgtctcagg aggatccaga ggtgcagttc aactggtacg tggatggcgt ggaggtgcac   1260
aatgctaaga ccaagccaag agaggagcag tttaattcca cataccgcgt ggtgagcgtg   1320
ctgaccgtgc tgcatcagga ttggctgaac ggcaaggagt ataagtgcaa ggtgtccaat   1380
aagggcctgc ccagctctat cgagaagaca atcagcaagg ctaagggaca gcctagggag   1440
ccacaggtgt acaccctgcc ccttctcag gaggagatga caagaaacca ggtgtccctg   1500
acctgtctgg tgaagggctt ctatccaagc gacatcgctg tggagtggga gtctaatggc   1560
cagcccgaga caattacaa gaccacacca cccgtgctgg actctgatgg ctccttcttt   1620
ctgtattcta ggctgacagt ggataagtcc cggtggcagg agggcaacgt gttttagctgc   1680 tctgtgatgc acgaggccct gcacaatcat tatacccaga agtccctgag cctgtctctg   1740
ggcaag                                                              1746
```

<210> SEQ ID NO 14
<211> LENGTH: 582
<212> TYPE: PRT
<213> ORGANISM: Artificial Sequence
<220> FEATURE:
<223> OTHER INFORMATION: Amino acid sequence of polypeptide chain H4

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95
```

```
Ala Ala Asp Leu Arg Glu Gly Phe Trp Asp Thr Gly Val Trp Asn Thr
            100                 105                 110

Trp Gly Gln Gly Thr Leu Val Thr Val Ser Ser Glu Pro Lys Ser Ser
        115                 120                 125

Asp Lys Thr His Thr Ser Pro Pro Ser Pro Glu Val Gln Leu Val Gln
    130                 135                 140

Ser Gly Ala Glu Val Lys Lys Pro Gly Ser Ser Val Lys Val Ser Cys
145                 150                 155                 160

Lys Ala Ser Gly Tyr Ser Phe Thr His His Trp Ile His Trp Val Arg
                165                 170                 175

Gln Ala Pro Gly Gln Gly Leu Glu Trp Met Gly Met Ile Asp Ala Ser
            180                 185                 190

Asp Ser Glu Thr Arg Leu Ser Gln Lys Phe Lys Asp Arg Val Thr Ile
        195                 200                 205

Thr Ala Asp Lys Ser Thr Ser Thr Ala Tyr Met Glu Leu Ser Ser Leu
    210                 215                 220

Arg Ser Glu Asp Thr Ala Val Tyr Tyr Cys Ala Arg Leu Gly Arg Tyr
225                 230                 235                 240

Tyr Phe Asp Tyr Trp Gly Gln Gly Thr Thr Val Thr Val Ser Ser Ala
                245                 250                 255

Ser Thr Lys Gly Pro Ser Val Phe Pro Leu Ala Pro Cys Ser Arg Ser
            260                 265                 270

Thr Ser Glu Ser Thr Ala Ala Leu Gly Cys Leu Val Lys Asp Tyr Phe
        275                 280                 285

Pro Glu Pro Val Thr Val Ser Trp Asn Ser Gly Ala Leu Thr Ser Gly
    290                 295                 300

Val His Thr Phe Pro Ala Val Leu Gln Ser Ser Gly Leu Tyr Ser Leu
305                 310                 315                 320

Ser Ser Val Val Thr Val Pro Ser Ser Ser Leu Gly Thr Lys Thr Tyr
                325                 330                 335

Thr Cys Asn Val Asp His Lys Pro Ser Asn Thr Lys Val Asp Lys Arg
            340                 345                 350

Val Glu Ser Lys Tyr Gly Pro Pro Cys Pro Pro Cys Pro Ala Pro Glu
        355                 360                 365

Phe Glu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser Gln Glu Asp Pro Glu Val Gln Phe Asn Trp Tyr Val Asp Gly
                405                 410                 415

Val Glu Val His Asn Ala Lys Thr Lys Pro Arg Glu Glu Gln Phe Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Gly Leu Pro
    450                 455                 460

Ser Ser Ile Glu Lys Thr Ile Ser Lys Ala Lys Gly Gln Pro Arg Glu
465                 470                 475                 480

Pro Gln Val Tyr Thr Leu Pro Pro Ser Gln Glu Glu Met Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
```

```
            515                 520                 525
Thr Pro Pro Val Leu Asp Ser Asp Gly Ser Phe Phe Leu Tyr Ser Arg
        530                 535                 540

Leu Thr Val Asp Lys Ser Arg Trp Gln Glu Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Leu Gly Lys
            580

<210> SEQ ID NO 15
<211> LENGTH: 1056
<212> TYPE: DNA
<213> ORGANISM: Artificial Sequence
<220> FEATURE:
<223> OTHER INFORMATION: DNA sequence of polypeptide chain L1

<400> SEQUENCE: 15
gagatcgtgc tgacccagtc tccagccaca ctgtctctgt ccccaggaga gagggccacc      60
ctgagctgcc gggcttctga aacgtgggc acatacatct cctggtatca gcagaagcca     120
ggacaggctc ctaggctgct gatctacggc gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga aaacacaaa gtctacgcct gcgaagtcac ccatcagggc     600
ctgagctcgc ccgtcacaaa gagcttcaac aggggagagt gtgaacctaa gtctagcgac     660
aaaactcata ccagcccccc tagtccagaa gtgcagctgg tggaatctgg cggcggactg     720
gtgcagcctg gcggctctct gcggctgtct tgtgccgtgt ccggcaacat ctacaaccgg     780
aacttcatgg gctggttccg gcaggccccc ggaaaaggcc gcgaaggcgt gtccgccatc     840
tacacgggca cctccagaac atattacgcc gacagcgtga aggtagatt caccatctcc     900 agagacaacg ccaagaacac cgtgtacctg cagatgaact ccctgagacc agaggacaca     960
gctgtgtact attgcgctgc tgatctgagg gatggcttct gggacaccgg cgtgtggaac    1020
acctggggcc agggcacact ggtcactgtg tcttcc                               1056

<210> SEQ ID NO 16
<211> LENGTH: 352
<212> TYPE: PRT
<213> ORGANISM: Artificial Sequence
<220> FEATURE:
<223> OTHER INFORMATION: Amino acid sequence of polypeptide chain L1

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45
```

Tyr Gly Ala Ser Asn Arg Tyr Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gly Glu Ser Tyr Gly His Leu Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Val Ser Gly Asn
                245                 250                 255

Ile Tyr Asn Arg Asn Phe Met Gly Trp Phe Arg Gln Ala Pro Gly Lys
            260                 265                 270

Gly Arg Glu Gly Val Ser Ala Ile Tyr Thr Gly Thr Ser Arg Thr Tyr
        275                 280                 285

Tyr Ala Asp Ser Val Lys Gly Arg Phe Thr Ile Ser Arg Asp Asn Ala
    290                 295                 300

Lys Asn Thr Val Tyr Leu Gln Met Asn Ser Leu Arg Pro Glu Asp Thr
305                 310                 315                 320

Ala Val Tyr Tyr Cys Ala Ala Asp Leu Arg Asp Gly Phe Trp Asp Thr
                325                 330                 335

Gly Val Trp Asn Thr Trp Gly Gln Gly Thr Leu Val Thr Val Ser Ser
            340                 345                 350

<210> SEQ ID NO 17
<211> LENGTH: 1056
<212> TYPE: DNA
<213> ORGANISM: Artificial Sequence
<220> FEATURE:
<223> OTHER INFORMATION: DNA sequence of polypeptide chain L2

<400> SEQUENCE: 17
gagatcgtgc tgacccagtc tccagccaca ctgtctctgt ccccaggaga gagggccacc      60
ctgagctgcc gggcttctga gaacgtgggc acatacatct cctggtatca gcagaagcca     120
ggacaggctc ctaggctgct gatctacggg gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360

-continued

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gtgaacctaa gtctagcgac    660
aaaactcata ccagccccc tagtccagag gtgcagctgg tcgagtctgg cggtggcctg     720
gttcagcccg gcggctccct gcggctgagc tgcgccgtgt ccggcaacat ctacaacaga    780
aacttcatgg gctggtttag acaggctcct ggcaagggac tggaaggcgt gtccgccatc    840
tacaccggca cctctcggac ttactacgcc gactctgtca agggcagatt caccatctcc    900
cgggacaact ccaagaacac agtgtatctg cagatgaaca gcctgagagc cgaggatacc    960
gctgtgtact actgcgctgc tgatctgaga gagggcttct gggacaccgg cgtgtggaat   1020
acctggggcc agggcaccct ggtgaccgtg tcttct                             1056
```

<210> SEQ ID NO 18
<211> LENGTH: 352
<212> TYPE: PRT
<213> ORGANISM: Artificial Sequence
<220> FEATURE:
<223> OTHER INFORMATION: Amino acid sequence of polypeptide chain L2

<400> SEQUENCE: 18

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240
```

-continued

```
Val Gln Pro Gly Gly Ser Leu Arg Leu Ser Cys Ala Val Ser Gly Asn
            245                 250                 255

Ile Tyr Asn Arg Asn Phe Met Gly Trp Phe Arg Gln Ala Pro Gly Lys
        260                 265                 270

Gly Leu Glu Gly Val Ser Ala Ile Tyr Thr Gly Thr Ser Arg Thr Tyr
    275                 280                 285

Tyr Ala Asp Ser Val Lys Gly Arg Phe Thr Ile Ser Arg Asp Asn Ser
290                 295                 300

Lys Asn Thr Val Tyr Leu Gln Met Asn Ser Leu Arg Ala Glu Asp Thr
305                 310                 315                 320

Ala Val Tyr Tyr Cys Ala Ala Asp Leu Arg Glu Gly Phe Trp Asp Thr
                325                 330                 335

Gly Val Trp Asn Thr Trp Gly Gln Gly Thr Leu Val Thr Val Ser Ser
            340                 345                 350
```

<210> SEQ ID NO 19
<211> LENGTH: 1056
<212> TYPE: DNA
<213> ORGANISM: Artificial Sequence
<220> FEATURE:
<223> OTHER INFORMATION: DNA sequence of polypeptide chain L3

<400> SEQUENCE: 19

```
gaagtgcagc tggtggaatc tggcggcgga ctggtgcagc ctggcggctc tctgcggctg      60
tcttgtgccg tgtccggcaa catctacaac cggaacttca tgggctggtt ccggcaggcc     120
cccggaaaag gccgcgaagg cgtgtccgcc atctacacgg gcacctccag aacatattac     180
gccgacagcg tgaaaggtag attcaccatc tccagagaca cgccaagaa caccgtgtac      240
ctgcagatga actccctgag accagaggac acagctgtgt actattgcgc tgctgatctg     300
agggatggct tctgggacac cggcgtgtgg aacacctggg gccagggcac actggtcact     360
gtgtcttccg aacctaagtc tagcgacaaa actcatacca gccccctag tccagagatc      420
gtgctgaccc cagtctccag cacactgtct ctgtccccag agagagggc caccctgagc      480
tgccgggctt ctgagaacgt gggcacatac atctcctggt atcagcagaa gccaggacag     540
gctcctaggc tgctgatcta cggcgctagc aatagatata ccggcatccc tgctcgcttc     600
agcggatctg gatccggcac agactttacc ctgacaatct ccagcctgga gccagaggat     660
ttcgccgtgt actattgtgg cgagtcctac ggccacctgt atcctttgg cggcggcaca     720
aaggtggaga tcaagcgaac ggtggctgca ccatctgtct tcatcttccc gccatctgat     780
gagcagttga aatctggaac tgcctctgtt gtgtgcctgc tgaataactt ctatcccaga     840
gaggccaaag tacagtggaa ggtggataac gccctccaat cgggtaactc ccaggagagt     900
gtcacagagc aggacagcaa ggacagcacc tacagcctca gcagcaccct gacgctgagc     960
aaagcagact acgagaaaca caaagtctac gcctgcgaag tcacccatca gggcctgagc    1020
tcgcccgtca caaagagctt caacagggga gagtgt                             1056
```

<210> SEQ ID NO 20
<211> LENGTH: 352
<212> TYPE: PRT
<213> ORGANISM: Artificial Sequence
<220> FEATURE:
<223> OTHER INFORMATION: Amino acid sequence of polypeptide chain L3

<400> SEQUENCE: 20

```
Glu Val Gln Leu Val Glu Ser Gly Gly Gly Leu Val Gln Pro Gly Gly
1               5                   10                  15
```

Ser Leu Arg Leu Ser Cys Ala Val Ser Gly Asn Ile Tyr Asn Arg Asn
                 20                  25                  30

Phe Met Gly Trp Phe Arg Gln Ala Pro Gly Lys Gly Arg Glu Gly Val
             35                  40                  45

Ser Ala Ile Tyr Thr Gly Thr Ser Arg Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Pro Lys Ser Ser
            115                 120                 125

Asp Lys Thr His Thr Ser Pro Pro Ser Pro Glu Ile Val Leu Thr Gln
130                 135                 140

Ser Pro Ala Thr Leu Ser Leu Ser Pro Gly Glu Arg Ala Thr Leu Ser
145                 150                 155                 160

Cys Arg Ala Ser Glu Asn Val Gly Thr Tyr Ile Ser Trp Tyr Gln Gln
                165                 170                 175

Lys Pro Gly Gln Ala Pro Arg Leu Leu Ile Tyr Gly Ala Ser Asn Arg
            180                 185                 190

Tyr Thr Gly Ile Pro Ala Arg Phe Ser Gly Ser Gly Ser Gly Thr Asp
            195                 200                 205

Phe Thr Leu Thr Ile Ser Ser Leu Glu Pro Glu Asp Phe Ala Val Tyr
210                 215                 220

Tyr Cys Gly Glu Ser Tyr Gly His Leu Tyr Thr Phe Gly Gly Gly Thr
225                 230                 235                 240

Lys Val Glu Ile Lys Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
            275                 280                 285

Asp Asn Ala Leu Gln Ser Gly Asn Ser Gln Glu Ser Val Thr Glu Gln
290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

<210> SEQ ID NO 21
<211> LENGTH: 1056
<212> TYPE: DNA
<213> ORGANISM: Artificial Sequence
<220> FEATURE:
<223> OTHER INFORMATION: DNA sequence of polypeptide chain L4

<400> SEQUENCE: 21
gaggtgcagc tggtcgagtc tggcggtggc ctggttcagc ccggcggctc cctgcggctg      60
agctgcgccg tgtccggcaa catctacaac agaaacttca tgggctggtt tagacaggct     120
cctggcaagg gactggaagg cgtgtccgcc atctacaccg gcacctctcg gacttactac     180

```
gccgactctg tcaagggcag attcaccatc tcccgggaca actccaagaa cacagtgtat    240
ctgcagatga acagcctgag agccgaggat accgctgtgt actactgcgc tgctgatctg    300
agagagggct tctgggacac cggcgtgtgg aatacctggg gccagggcac cctggtgacc    360
gtgtcttctg aacctaagtc tagcgacaaa actcatacca ccccccctag tccagagatc    420
gtgctgaccc agtctccagc cacactgtct ctgtccccag agagagggc cccctgagc    480 tgccgggctt ctgagaacgt gggcacatac atctcctggt atcagcagaa gccaggacag    540
gctcctaggc tgctgatcta cggcgctagc aatagatata ccggcatccc tgctcgcttc    600
agcggatctg gatccggcac agactttacc ctgacaatct ccagcctgga gccagaggat    660
ttcgccgtgt actattgtgg cgagtcctac ggccacctgt atcctttgg cggcggcaca    720 aaggtggaga tcaagcgaac ggtggctgca ccatctgtct tcatcttccc gccatctgat    780
gagcagttga atctggaac tgcctctgtt gtgtgcctgc tgaataactt ctatcccaga    840
gaggccaaag tacagtggaa ggtggataac gccctccaat cgggtaactc ccaggagagt    900
gtcacagagc aggacagcaa ggacagcacc tacagcctca gcagcaccct gacgctgagc    960
aaagcagact acgagaaaca caaagtctac gcctgcgaag tcacccatca gggcctgagc    1020
tcgcccgtca caaagagctt caacagggga gagtgt                            1056
```

<210> SEQ ID NO 22
<211> LENGTH: 352
<212> TYPE: PRT
<213> ORGANISM: Artificial Sequence
<220> FEATURE:
<223> OTHER INFORMATION: Amino acid sequence of polypeptide chain L4

<400> SEQUENCE: 22

```
Glu Val Gln Leu Val Glu Ser Gly Gly Gly Leu Val Gln Pro Gly Gly
1               5                  10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser Glu Pro Lys Ser Ser
        115                 120                 125

Asp Lys Thr His Thr Ser Pro Pro Ser Pro Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Glu Asn Val Gly Thr Tyr Ile Ser Trp Tyr Gln Gln
                165                 170                 175

Lys Pro Gly Gln Ala Pro Arg Leu Leu Ile Tyr Gly Ala Ser Asn Arg
            180                 185                 190

Tyr Thr Gly Ile Pro Ala Arg Phe Ser Gly Ser Gly Ser Gly Thr Asp
        195                 200                 205
```

```
Phe Thr Leu Thr Ile Ser Ser Leu Glu Pro Glu Asp Phe Ala Val Tyr
        210                 215                 220

Tyr Cys Gly Glu Ser Tyr Gly His Leu Tyr Thr Phe Gly Gly Gly Thr
225                 230                 235                 240

Lys Val Glu Ile Lys Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
        290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350
```

<210> SEQ ID NO 23
<211> LENGTH: 1746
<212> TYPE: DNA
<213> ORGANISM: Artificial Sequence
<220> FEATURE:
<223> OTHER INFORMATION: DNA sequence of polypeptide chain H5

<400> SEQUENCE: 23

```
gaggtgcagc tggtgcagtc cggagctgag gtgaagaagc caggatccag cgtgaaggtg      60
agctgcaagg ctagcggcta ctctttcacc caccattgga tccactgggt gaggcaggct     120
cctggacagg gactggagtg gatgggcatg atcgacgctt ccgatagcga gacaagactg     180
tctcagaagt ttaaggaccg cgtgaccatc acagccgata gtctacctc cacagcttac     240
atggagctgt cttccctgag atccgaggac accgccgtgt actattgtgc taggctgggc     300
cggtactatt tcgattattg gggccagggc accacagtga cagtgagctc tgccagcaca     360
aagggccctt ccgtgttccc actggctccc tgctccagaa gcacatctga gtccaccgcc     420
gctctgggct gtctggtgaa ggactacttc cctgagccag tgaccgtgtc ctggaacagc     480
ggcgccctga catctggcgt gcacaccttt ccagctgtgc tgcagtccag cggcctgtac     540
tccctgtctt ccgtggtgac agtgcccagc tcttccctgg gcaccaagac atatacctgc     600
aacgtggacc ataagccttc caataccaag gtggataaga gggtggagag caagtacgga     660
ccaccttgcc caccatgtcc agctcctgag tttgagggag gaccatccgt gttcctgttt     720
cctccaaagc ctaaggacac cctgatgatc agccggacac tgaggtgac ctgcgtggtg     780
gtggacgtgt ctcaggagga tccagaggtg cagttcaact ggtacgtgga tggcgtggag     840
gtgcacaatg ctaagaccaa gccaagagag gagcagttta attccacata ccgcgtggtg     900
agcgtgctga ccgtgctgca tcaggattgg ctgaacggca aggagtataa gtgcaaggtg     960
tccaataagg gcctgcccag ctctatcgag aagacaatca gcaaggctaa gggacagcct    1020
agggagccac aggtgtacac cctgccccct tctcaggagg agatgacaaa gaaccaggtg    1080
tccctgacct gtctggtgaa gggcttctat ccaagcgaca tcgctgtgga gtgggagtct    1140
aatggccagc ccgagaacaa ttacaagacc acaccacccg tgctggactc tgatggctcc    1200
ttctttctgt attctaggct gacagtggat aagtcccggt ggcaggaggg caacgtgttt    1260
```

```
agctgctctg tgatgcacga ggccctgcac aatcattata cccagaagtc cctgagcctg    1320
tctctgggca agggtggagg cggtagtgga ggcggtggtt caggcggagg cggatctgaa    1380
gtgcagctgg tggaatctgg cggcggactg gtgcagcctg gcggctctct gcggctgtct    1440
tgtgccgtgt ccggcaacat ctacaaccgg aacttcatgg gctggttccg gcaggccccc    1500
ggaaaaggcc gcgaaggcgt gtccgccatc tacacgggca cctccagaac atattacgcc    1560
gacagcgtga aagtagatt caccatctcc agagacaacg ccaagaacac cgtgtacctg    1620
cagatgaact ccctgagacc agaggacaca gctgtgtact attgcgctgc tgatctgagg    1680
gatggcttct gggacaccgg cgtgtggaac cctggggcc agggcacact ggtcactgtg    1740
tcttcc                                                              1746

<210> SEQ ID NO 24
<211> LENGTH: 582
<212> TYPE: PRT
<213> ORGANISM: Artificial Sequence
<220> FEATURE:
<223> OTHER INFORMATION: Amino acid sequence of polypeptide chain H5

<400> SEQUENCE: 24

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
                20                  25                  30

Trp Ile His Trp Val Arg Gln Ala Pro Gly Gln Gly Leu Glu Trp Met
            35                  40                  45

Gly Met Ile Asp Ala Ser Asp Ser Glu Thr Arg Leu Ser Gln Lys Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270
```

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Gly Ser Gly Gly Gly Gly Ser Glu Val Gln Leu Val
    450                 455                 460

Glu Ser Gly Gly Gly Leu Val Gln Pro Gly Gly Ser Leu Arg Leu Ser
465                 470                 475                 480

Cys Ala Val Ser Gly Asn Ile Tyr Asn Arg Asn Phe Met Gly Trp Phe
                485                 490                 495

Arg Gln Ala Pro Gly Lys Gly Arg Glu Gly Val Ser Ala Ile Tyr Thr
            500                 505                 510

Gly Thr Ser Arg Thr Tyr Tyr Ala Asp Ser Val Lys Gly Arg Phe Thr
        515                 520                 525

Ile Ser Arg Asp Asn Ala Lys Asn Thr Val Tyr Leu Gln Met Asn Ser
530                 535                 540

Leu Arg Pro Glu Asp Thr Ala Val Tyr Tyr Cys Ala Ala Asp Leu Arg
545                 550                 555                 560

Asp Gly Phe Trp Asp Thr Gly Val Trp Asn Thr Trp Gly Gln Gly Thr
                565                 570                 575

Leu Val Thr Val Ser Ser
            580

<210> SEQ ID NO 25
<211> LENGTH: 1056
<212> TYPE: DNA
<213> ORGANISM: Artificial Sequence
<220> FEATURE:
<223> OTHER INFORMATION: DNA sequence of polypeptide chain H6

<400> SEQUENCE: 25
gaagtgcagc tggtggaatc tggcggcgga ctggtgcagc ctggcggctc tctgcggctg    60
tcttgtgccg tgtccggcaa catctacaac cggaacttca tgggctggtt ccggcaggcc   120
cccggaaaag gccgcgaagg cgtgtccgcc atctacaccg gcacctccag aacatattac   180
gccgacagcg tgaaaggtag attcaccatc tccagagaca acgccaagaa caccgtgtac   240

```
ctgcagatga actccctgag accagaggac acagctgtgt actattgcgc tgctgatctg    300
agggatggct tctgggacac cggcgtgtgg aacacctggg ccagggcac actggtcact     360
gtgtcttccg agagcaagta cggaccacct tgcccaccat gtccagctcc tgagtttgag    420
ggaggaccat ccgtgttcct gtttcctcca aagcctaagg acaccctgat gatcagccgg    480
acacctgagg tgacctgcgt ggtggtggac gtgtctcagg aggatccaga ggtgcagttc    540
aactggtacg tggatggcgt ggaggtgcac aatgctaaga ccaagccaag agaggagcag    600
tttaattcca cataccgcgt ggtgagcgtg ctgaccgtgc tgcatcagga ttggctgaac    660
ggcaaggagt ataagtgcaa ggtgtccaat aagggcctgc ccagctctat cgagaagaca    720
atcagcaagg ctaagggaca gcctagggag ccacaggtgt acaccctgcc ccttctcag    780
gaggagatga caagaaacca ggtgtccctg acctgtctgg tgaagggctt ctatccaagc    840
gacatcgctg tggagtggga gtctaatggc cagcccgaga caattacaa gaccacacca    900
cccgtgctgg actctgatgg ctccttcttt ctgtattcta ggctgacagt ggataagtcc    960
cggtggcagg agggcaacgt gtttagctgc tctgtgatgc acgaggccct gcacaatcat    1020
tatacccaga agtccctgag cctgtctctg ggcaag                             1056
```

<210> SEQ ID NO 26
<211> LENGTH: 352
<212> TYPE: PRT
<213> ORGANISM: Artificial Sequence
<220> FEATURE:
<223> OTHER INFORMATION: Amino acid sequence of polypeptide chain H6

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Arg Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220
```

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
                340                 345                 350

<210> SEQ ID NO 27
<211> LENGTH: 1056
<212> TYPE: DNA
<213> ORGANISM: Artificial Sequence
<220> FEATURE:
<223> OTHER INFORMATION: DNA sequence of polypeptide chain H7

<400> SEQUENCE: 27
gaggtgcagc tggtcgagtc tggcggtggc ctggttcagc ccggcggctc cctgcggctg      60
agctgcgccg tgtccggcaa catctacaac agaaacttca tgggctggtt tagacaggct     120
cctggcaagg gactggaagg cgtgtccgcc atctacaccg gcacctctcg gacttactac     180
gccgactctg tcaagggcag attcaccatc tcccgggaca actccaagaa cacagtgtat     240
ctgcagatga acagcctgag agccgaggat accgctgtgt actactgcgc tgctgatctg     300
agagagggct tctgggacac cggcgtgtgg aatacctggg gccagggcac cctggtgacc     360
gtgtcttctg agcaagta cggaccacct tgcccaccat gtccagctcc tgagtttgag      420
ggaggaccat ccgtgttcct gtttcctcca aagcctaagg acaccctgat gatcagccgg     480
acacctgagg tgacctgcgt ggtggtggac gtgtctcagg aggatccaga ggtgcagttc     540
aactggtacg tggatggcgt ggaggtgcac aatgctaaga ccaagccaag agaggagcag     600
tttaattcca cataccgcgt ggtgagcgtg ctgaccgtgc tgcatcagga ttggctgaac     660
ggcaaggagt ataagtgcaa ggtgtccaat aagggcctgc ccagctctat cgagaagaca     720
atcagcaagg ctaagggaca gcctagggag ccacaggtgt acaccctgcc cccttctcag     780
gaggagatga caaagaacca ggtgtccctg acctgtctgg tgaagggctt ctatccaagc     840
gacatcgctg tggagtggga gtctaatggc cagcccgaga caattacaa gaccacacca     900 cccgtgctgg actctgatgg ctccttcttt ctgtattcta ggctgacagt ggataagtcc     960
cggtggcagg agggcaacgt gtttagctgc tctgtgatgc acgaggccct gcacaatcat    1020
tatacccaga gtccctgag cctgtctctg ggcaag                                1056

<210> SEQ ID NO 28
<211> LENGTH: 352
<212> TYPE: PRT
<213> ORGANISM: Artificial Sequence
<220> FEATURE:
<223> OTHER INFORMATION: Amino acid sequence of polypeptide chain H7

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Glu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
            340                 345                 350

<210> SEQ ID NO 29
<211> LENGTH: 369
<212> TYPE: DNA
<213> ORGANISM: Artificial Sequence
<220> FEATURE:
<223> OTHER INFORMATION: DNA sequence of PD-1a sdAb

<400> SEQUENCE: 29
gaagtgcagc tggtggaatc tggcggcgga ctggtgcagc ctggcggctc tctgcggctg    60

```
tcttgtgccg tgtccggcaa catctacaac cggaacttca tgggctggtt ccggcaggcc    120
cccggaaaag gccgcgaagg cgtgtccgcc atctacacgg gcacctccag aacatattac    180
gccgacagcg tgaaaggtag attcaccatc tccagagaca acgccaagaa caccgtgtac    240
ctgcagatga actccctgag accagaggac acagctgtgt actattgcgc tgctgatctg    300
agggatggct ctgggacac cggcgtgtgg aacacctggg gccagggcac actggtcact    360
gtgtcttcc                                                           369
```

<210> SEQ ID NO 30
<211> LENGTH: 123
<212> TYPE: PRT
<213> ORGANISM: Artificial Sequence
<220> FEATURE:
<223> OTHER INFORMATION: Amino acid sequence of PD-1a sdAb

<400> SEQUENCE: 30

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Arg Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser
        115                 120
```

<210> SEQ ID NO 31
<211> LENGTH: 369
<212> TYPE: DNA
<213> ORGANISM: Artificial Sequence
<220> FEATURE:
<223> OTHER INFORMATION: DNA sequence of PD-1b sdAb

<400> SEQUENCE: 31

```
gaggtgcagc tggtcgagtc tggcggtggc ctggttcagc ccggcggctc cctgcggctg     60
agctgcgccg tgtccggcaa catctacaac agaaacttca tgggctggtt tagacaggct    120
cctggcaagg gactggaagg cgtgtccgcc atctacaccg gcacctctcg acttactac     180 gccgactctg tcaagggcag attcaccatc tcccgggaca actccaagaa cacagtgtat    240
ctgcagatga acagcctgag agccgaggat accgctgtgt actactgcgc tgctgatctg    300
agagagggct ctgggacac cggcgtgtgg aatacctggg gccagggcac cctggtgacc    360
gtgtcttct                                                           369
```

<210> SEQ ID NO 32
<211> LENGTH: 123
<212> TYPE: PRT
<213> ORGANISM: Artificial Sequence
<220> FEATURE:
<223> OTHER INFORMATION: Amino acid sequence of PD-1b sdAb

<400> SEQUENCE: 32

Glu Val Gln Leu Val Glu Ser Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser
        115                 120

<210> SEQ ID NO 33
<211> LENGTH: 10
<212> TYPE: PRT
<213> ORGANISM: Artificial Sequence
<220> FEATURE:
<223> OTHER INFORMATION: Heavy chain CDR1 sequence of anti-CD47 antibody

<400> SEQUENCE: 33

Gly Tyr Ser Phe Thr His His Trp Ile His
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Heavy chain CDR2 sequence of anti-CD47 antibody

<400> SEQUENCE: 34

Met Ile Asp Ala Ser Asp Ser Glu Thr Arg Leu Ser Gln Lys Phe Lys
1               5                   10                  15

Asp

<210> SEQ ID NO 35
<211> LENGTH: 8
<212> TYPE: PRT
<213> ORGANISM: Artificial Sequence
<220> FEATURE:
<223> OTHER INFORMATION: Heavy chain CDR3 sequence of anti-CD47 antibody

<400> SEQUENCE: 35

Leu Gly Arg Tyr Tyr Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Light chain CDR1 sequence of anti-CD47 antibody

<400> SEQUENCE: 36

Arg Ala Ser Glu Asn Val Gly Thr Tyr Ile Ser
1               5                   10

```
<210> SEQ ID NO 37
<211> LENGTH: 7
<212> TYPE: PRT
<213> ORGANISM: Artificial Sequence
<220> FEATURE:
<223> OTHER INFORMATION: Light chain CDR2 sequence of anti-CD47 antibody

<400> SEQUENCE: 37

Gly Ala Ser Asn Arg Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Light chain CDR3 sequence of anti-CD47 antibody

<400> SEQUENCE: 38

Gly Glu Ser Tyr Gly His Leu Tyr Thr
1               5

<210> SEQ ID NO 39
<211> LENGTH: 10
<212> TYPE: PRT
<213> ORGANISM: Artificial Sequence
<220> FEATURE:
<223> OTHER INFORMATION: CDR1 amino acid sequence of PD-1a sdAb

<400> SEQUENCE: 39

Gly Asn Ile Tyr Asn Arg Asn Phe Met Gly
1               5                   10

<210> SEQ ID NO 40
<211> LENGTH: 17
<212> TYPE: PRT
<213> ORGANISM: Artificial Sequence
<220> FEATURE:
<223> OTHER INFORMATION: CDR2 amino acid sequence of PD-1a sdAb

<400> SEQUENCE: 40

Ala Ile Tyr Thr Gly Thr Ser Arg Thr Tyr Tyr Ala Asp Ser Val Lys
1               5                   10                  15

Gly

<210> SEQ ID NO 41
<211> LENGTH: 14
<212> TYPE: PRT
<213> ORGANISM: Artificial Sequence
<220> FEATURE:
<223> OTHER INFORMATION: CDR3 amino acid sequence of PD-1a sdAb

<400> SEQUENCE: 41

Asp Leu Arg Asp Gly Phe Trp Asp Thr Gly Val Trp Asn Thr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: CDR1 amino acid sequence of PD-1b sdAb

<400> SEQUENCE: 42

Gly Asn Ile Tyr Asn Arg Asn Phe Met Gly
```

<210> SEQ ID NO 43
<211> LENGTH: 17
<212> TYPE: PRT
<213> ORGANISM: Artificial Sequence
<220> FEATURE:
<223> OTHER INFORMATION: CDR2 amino acid sequence ofPD-1b sdAb

<400> SEQUENCE: 43

Ala Ile Tyr Thr Gly Thr Ser Arg Thr Tyr Tyr Ala Asp Ser Val Lys
1               5                   10                  15
Gly

<210> SEQ ID NO 44
<211> LENGTH: 14
<212> TYPE: PRT
<213> ORGANISM: Artificial Sequence
<220> FEATURE:
<223> OTHER INFORMATION: CDR3 amino acid sequence of PD-1b sdAb

<400> SEQUENCE: 44

Asp Leu Arg Glu Gly Phe Trp Asp Thr Gly Val Trp Asn Thr
1               5                   10

<210> SEQ ID NO 45
<211> LENGTH: 45
<212> TYPE: DNA
<213> ORGANISM: Artificial Sequence
<220> FEATURE:
<223> OTHER INFORMATION: DNA sequence of E-Linker

<400> SEQUENCE: 45
gaacctaagt ctagcgacaa aactcatacc agccccccta gtcca          45

<210> SEQ ID NO 46
<211> LENGTH: 15
<212> TYPE: PRT
<213> ORGANISM: Artificial Sequence
<220> FEATURE:
<223> OTHER INFORMATION: Amino acid sequence of E-Linker

<400> SEQUENCE: 46

Glu Pro Lys Ser Ser Asp Lys Thr His Thr Ser Pro Pro Ser Pro
1               5                   10                  15

<210> SEQ ID NO 47
<211> LENGTH: 45
<212> TYPE: DNA
<213> ORGANISM: Artificial Sequence
<220> FEATURE:
<223> OTHER INFORMATION: DNA sequence of G15-Linker

<400> SEQUENCE: 47
ggtggaggcg gtagtggagg cggtggttca ggcggaggcg gatct          45

<210> SEQ ID NO 48
<211> LENGTH: 15
<212> TYPE: PRT
<213> ORGANISM: Artificial Sequence
<220> FEATURE:
<223> OTHER INFORMATION: Amino acid sequence of G15-Linker

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 687
<212> TYPE: DNA
<213> ORGANISM: Artificial Sequence
<220> FEATURE:
<223> OTHER INFORMATION: DNA sequence of IgG4 Fc

<400> SEQUENCE: 49

```
gagagcaagt acggaccacc ttgcccacca tgtccagctc ctgagtttga gggaggacca      60
tccgtgttcc tgtttcctcc aaagcctaag gacaccctga tgatcagccg gacacctgag     120
gtgacctgcg tggtggtgga cgtgtctcag gaggatccag aggtgcagtt caactggtac     180
gtggatggcg tggaggtgca caatgctaag accaagccaa gagaggagca gtttaattcc     240
acataccgcg tggtgagcgt gctgaccgtg ctgcatcagg attggctgaa cggcaaggag     300
tataagtgca aggtgtccaa taagggcctg cccagctcta tcgagaagac aatcagcaag     360
gctaagggac agcctaggga gccacaggtg tacacccctg ccccttctca ggaggagatg     420
acaaagaacc aggtgtccct gacctgtctg gtgaagggct ctatccaagc gacatcgct     480
gtggagtggg agtctaatgg ccagcccgag aacaattaca agaccacacc acccgtgctg     540
gactctgatg gctccttctt tctgtattct aggctgacag tggataagtc ccggtggcag     600
gagggcaacg tgtttagctg ctctgtgatg cacgaggccc tgcacaatca ttatacccag     660
aagtccctga gcctgtctct gggcaag                                         687
```

<210> SEQ ID NO 50
<211> LENGTH: 229
<212> TYPE: PRT
<213> ORGANISM: Artificial Sequence
<220> FEATURE:
<223> OTHER INFORMATION: Amino acid sequence of IgG4 Fc

<400> SEQUENCE: 50

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
```

```
              180              185              190
Thr Val Asp Lys Ser Arg Trp Gln Glu Gly Asn Val Phe Ser Cys Ser
            195                200              205

Val Met His Glu Ala Leu His Asn His Tyr Thr Gln Lys Ser Leu Ser
    210              215              220

Leu Ser Leu Gly Lys
225
```